US009834754B2

(12) United States Patent
Keller et al.

(10) Patent No.: US 9,834,754 B2
(45) Date of Patent: Dec. 5, 2017

(54) POPULATIONS OF HEMATOPOIETIC PROGENITORS AND METHODS OF ENRICHING STEM CELLS THEREFOR

(71) Applicants: University Health Network, Toronto (CA); Sunnybrook Research Institute, Toronto (CA)

(72) Inventors: Gordon Keller, Toronto (CA); Juan Carlos Zuniga-Pflucker, Toronto (CA); Marion J. Kennedy, Toronto (CA); Christopher Michael Sturgeon, Toronto (CA); Andrea Ditadi, Toronto (CA); Geneve Sheandra Awong, Toronto (CA)

(73) Assignees: UNIVERSITY HEALTH NETWORK, Toronto (CA); SUNNYBROOK RESEARCH INSTITUTE, Toronto (CA)

( * ) Notice: Subject to any disclaimer, the term of this patent is extended or adjusted under 35 U.S.C. 154(b) by 0 days.

(21) Appl. No.: 14/359,517

(22) PCT Filed: Nov. 21, 2012

(86) PCT No.: PCT/CA2012/001076
§ 371 (c)(1),
(2) Date: May 20, 2014

(87) PCT Pub. No.: WO2013/075222
PCT Pub. Date: May 30, 2013

(65) Prior Publication Data
US 2014/0322808 A1 Oct. 30, 2014

Related U.S. Application Data

(60) Provisional application No. 61/562,094, filed on Nov. 21, 2011.

(51) Int. Cl.
*C12N 5/00* (2006.01)
*C12N 5/0789* (2010.01)
*G01N 33/569* (2006.01)

(52) U.S. Cl.
CPC ..... *C12N 5/0647* (2013.01); *G01N 33/56972* (2013.01); *C12N 2500/24* (2013.01); *C12N 2500/35* (2013.01); *C12N 2500/38* (2013.01); *C12N 2501/105* (2013.01); *C12N 2501/115* (2013.01); *C12N 2501/125* (2013.01); *C12N 2501/14* (2013.01); *C12N 2501/145* (2013.01); *C12N 2501/155* (2013.01); *C12N 2501/16* (2013.01); *C12N 2501/165* (2013.01); *C12N 2501/2303* (2013.01); *C12N 2501/2306* (2013.01); *C12N 2501/2307* (2013.01); *C12N 2501/2311* (2013.01); *C12N 2501/26* (2013.01); *C12N 2502/1394* (2013.01); *C12N 2506/02* (2013.01); *C12N 2506/45* (2013.01); *G01N 2333/70596* (2013.01)

(58) Field of Classification Search
None
See application file for complete search history.

(56) References Cited

FOREIGN PATENT DOCUMENTS

WO 2010099539 A1 9/2010

OTHER PUBLICATIONS

Moore et al. J Immunol 1994;153:4978-87.*
Wang et al. Cell Res 2012;22:194-207, published online Aug. 23, 2011.*
Awong et al., "Characterization in vitro and engraftment potential in vivo of human progenitor T cells generated from hematopoietic stem cells," (2009), Blood 114, 972-982.
Bertrand et al., "Characterization of purified intraembryonic hematopoietic stem cells as a tool to define their site of origin," (2005), Proceedings of the National Academy of Sciences of the United States of America 102, 134-139.
Chadwick et al., "Cytokines and BMP-4 promote hematopoietic differentiation of human embryonic stem cells," (2003) Blood 102, 906-915.
Choi et al., "Identification of the hemogenic endothelial progenitor and its direct precursor in human pluripotent stem cell differentiation cultures," (2012) Cell reports 2, 553-567.
Choi et al., "Identification of the hemogenic endothelial progenitor and its direct precursor in human pluripotent stem cell differentiation cultures," (2012), 53rd ASH Annual Meeting and Exposition; Poster 1277.
Inman et al., "SB-431542 is a potent and specific inhibitor of transforming growth factor-beta superfamily type I activin receptor-like kinase (ALK) receptors ALK4, ALK5, and ALK7," (2002), Mol Pharmacol 62, 65-74.
Irion et al., "Temporal specification of blood progenitors from mouse embryonic stem cells and induced pluripotent stem cells," (2010), Development (Cambridge, England) 137, 2829-2839.
Kaufman et al., "Hematopoietic colony-forming cells derived from human embryonic stem cells," (2001), Proceedings of the National Academy of Sciences of the United States of America 98, 10716-10721.
Klimchenko et al., "A common bipotent progenitor generates the erythroid and megakaryocyte lineages in embryonic stem cell-derived primitive hematopoiesis," (2009), Blood 114, 1506-1517.
La Motte-Mohs et al., "Induction of T-cell development from human cord blood hematopoietic stem cells by Delta-like 1 in vitro," (2005), Blood 105, 1431-1439.

(Continued)

*Primary Examiner* — Janice Li
(74) *Attorney, Agent, or Firm* — J.A. Lindeman & Co. PLLC

(57) ABSTRACT

There is described herein a method of enriching a population of stem cells for hematopoietic progenitors. The method comprises inducing hematopoietic differentiation in a population of human embryonic stem cells or human induced pluripotent stem cells; sorting the population based on expression of CD43 and at least one of CD34, CD31 and CD144; and selecting a fraction that is at least one of CD34+CD43−, CD31+CD43− and CD144+CD43−. Also provided are populations of hematopoietic progenitors obtained by the methods described herein.

14 Claims, 10 Drawing Sheets

(56) References Cited

OTHER PUBLICATIONS

Ledran et al., "Efficient hematopoietic differentiation of human embryonic stem cells on stromal cells derived from hematopoietic niches," (2008), Cell stem cell 3, 85-98.
Lu et al., "Enhanced generation of hematopoietic cells from human hepatocarcinoma cell-stimulated human embryonic and induced pluripotent stem cells," (2009), Experimental hematology 37, 924-936.
Nostro et al., "Wnt, activin, and BMP signaling regulate distinct stages in the developmental pathway from embryonic stem cells to blood," (2008), Cell stem cell 2, 60-71.
Notta et al., "Isolation of single human hematopoietic stem cells capable of long-term multilineage engraftment," (2011), Science New York, vol. 333, 218-221.
Oberlin et al., "Blood-forming potential of vascular endothelium in the human embryo," (2002), Development (Cambridge, England) 129, 4147-4157.
Palis et al., "Primitive erythropoiesis in the mammalian embryo," (2010), Int. J. Dev. Biol. 54, 1011-1018.
Park et al., "Reprogramming of human somatic cells to pluripotency with defined factors," (2008), Nature, vol. 451, 141-146.
Pearson et al., "The stepwise specification of embryonic stem cells to hematopoietic fate is driven by sequential exposure to Bmp4, activin A, bFGF and VEGF, " (2008), Development (Cambridge, England) 135, 1525-1535.
Pick et al., "Differentiation of human embryonic stem cells in serum-free medium reveals distinct roles for bone morphogenetic protein 4, vascular endothelial growth factor, stem cell factor, and fibroblast growth factor 2 in hematopoiesis," (2007), Stem Cells 25, 2206-2214.
Sumi et al., "Defining early lineage specification of human embryonic stem cells by the orchestrated balance of canonical Wnt/beta-catenin, Activin/Nodal and BMP signaling," (2008), Development (Cambridge, England) 135, 2969-2979.
Timmermans et al., "Generation of T cells from human embryonic stem cell-derived hematopoietic zones," (2009), J Immunol 182, 6879-6888.
Vijayaragavan et al., "Noncanonical Wnt signaling orchestrates early developmental events toward hematopoietic cell fate from human embryonic stem cells," (2009), Cell stem cell 4, 248-262.
Vodyanik et al., "Leukosialin (CD43) defines hematopoietic progenitors in human embryonic stem cell differentiation cultures," (2006), Blood 108, 2095-2105.
Wang et al., "Generation of hematopoietic repopulating cells from human embryonic stem cells independent of ectopic HOXB4 expression," (2005), The Journal of experimental medicine, vol. 201, No. 10, 1603-1614.

Yoshimoto et al., "Autonomous murine T-cell progenitor production in the extra-embryonic yolk sac before HSC emergence," (2012), Blood 119, 5706-5714.
Yu et al., "Retinoic acid enhances the generation of hematopoietic progenitors from human embryonic stem cell-derived hematovascular precursors," (2010), Blood 116, 4786-4794.
Zambidis et al., "Hematopoietic differentiation of human embryonic stem cells progresses through sequential hematoendothelial, primitive, and definitive stages resembling human yolk sac development," (2005), Blood 106, 860-870.
Yoshimoto et al., "Embryonic day 9 yolk sac and intra-embryonic hemogenic endothelium independently generate a B-1 and marginal zone progenitor lacking B-2 potential," (2011), Proceedings of the National Academy of Sciences of the United States of America 108, 1468-1473.
Laurie et al., "Human pluripotent stem cells differentiated in fully defined medium generate hematopoietic CD34-and CD34+ progenitors with distinct characteristics," (2011), Plos One, Public Library of Science, US, vol. 6, No. 2, 8 pp.
Choi et al., " Hematopoietic and endothelial differentiation of human induced pluripotent stem cells," (2009), Stem Cells, vol. 27, No. 3, 559-567.
Supplementary European Search Report of EP Application No. 12851240, dated Feb. 24, 2015.
International Preliminary Report on Patentability of International Application No. PCT/CA2012/001076, dated Feb. 28, 2013.
International Search Report and Written Opinion of International Application No. PCT/CA2012/001076, dated Mar. 5, 2013.
Technical Bulletin, "Culture of hematopoietic stem and progenitor cells,", StemCell Technologies, Dec. 2009, pp. 4-5.
Chica et al., "Human Pluripotent Stem Cells Differentiated in Fully Defined Medium Generate Hematopoietic CD34+ and CD34- Progenitors with Distinct Characteristics," PLoS One, Feb. 2011, vol. 6, Issue 2, e14733, pp. 1-8.
Chinese Office Action in corresponding application No. 201280056826.9, dated Aug. 19, 2016.
English translation of Chinese Office Action in corresponding application No. 201280056826.9.
Kennedy et al., "T Lymphocyte Potential Marks the Emergence of Definitive Hematopoietic Progenitors in Human Pluripotent Stem Cell Diffferentiation Cultures," Cell reportts 2, Dec. 27, 2012, pp. 1722-1735.
Sturgeon et al., "Wnt Signaling Controls the Specification of Definitive and Primitive Hematopoiesis From Human Pluripotent Stem Cells," HHS Public Access, Author manuscript, Nat. Biotechnol. 2014, pp. 1-22.
Vodyanik et al., "Human embryonic stem cell-derived CD34+ cells: efficient production in the coculture with OP9 stromal cells and analysis of lymphohematopoietic potential," Blood, Jan. 15, 2005, vol. 105, No. 2, pp. 617-626.

* cited by examiner

US 9,834,754 B2

POPULATIONS OF HEMATOPOIETIC PROGENITORS AND METHODS OF ENRICHING STEM CELLS THEREFOR

CROSS-REFERENCE TO RELATED APPLICATIONS

This application is a National Phase application under 35 U.S.C. §371 of International Application No. PCT/CA2012/001076, filed Nov. 21, 2012, which claims priority from U.S. Provisional Patent Application No. 61/562,094 filed Nov. 21, 2011, the content of each is hereby incorporated in its entirety.

FIELD OF THE INVENTION

The invention relates to populations of hematopoietic progenitors and methods for enriching populations of stem cells for hematopoietic progenitors.

BACKGROUND OF THE INVENTION

The ability to generate hematopoietic stem cells (HSCs) from human pluripotent stem cells (PSCs), embryonic (hESCs) and induced pluripotent stem cells (hiPSC) would enable the production of unlimited numbers of patient-matched stem cells for transplantation and the derivation of novel in vitro models for studying human hematopoietic development and disease. Numerous studies have shown that it is possible to derive hematopoietic lineage cells from hPSCs either by co-culturing them with stromal cells in serum-based media, or by directing their differentiation with specific morphogens in defined serum-free media (Chadwick et al., 2003; Davis et al., 2008; Kaufman et al., 2001; Kennedy et al., 2007; Ledran et al., 2008; Ng et al., 2005; Pick et al., 2007; Vodyanik et al., 2006; Yu et al., 2010; Zambidis et al., 2005). While these approaches yield a broad spectrum of hematopoietic progenitors, transplantation of the progeny from such cultures into immunocompromised mice has typically resulted in low levels of engraftment often restricted to the myeloid lineages (Lu et al., 2009; Tian et al., 2006; Wang et al., 2005). These findings suggest that the conditions used for hematopoietic differentiation do not support the development of HSCs. A major factor contributing to the failure in generating HSCs from hPSCs is the complexity of the embryonic hematopoietic system, which consists of at least two distinct programs, only one of which gives rise to HSCs.

HSCs are generated from the definitive hematopoietic program and develop from a specialized population of endothelial cells, known as hemogenic endothelium (HE; (Dzierzak and Speck, 2008)). In the mouse, HE is specified at different sites within the developing vasculature, of which the best characterized is the para-aortic splanchnopleura (P-Sp)/aorta-gonad-mesonephros (AGM) region found in the caudal portion of the embryo. The mouse HE is characterized by expression of a panel of hematopoietic and endothelial markers, including VE-cadherin (VE-cad), Sca-1, c-Kit, CD34, Runx1, Scl, Gata2 and Lmo2 (reviewed in (Dzierzak and Speck, 2008)). HSCs are first detectable in the AGM region at E10.5 and are characterized by the acquisition of low CD45 expression in addition to the above set of markers (Bertrand et al., 2005; Taoudi and Medvinsky, 2007; Yokomizo and Dzierzak, 2010). The human P-Sp/AGM region is also a site of definitive hematopoiesis as it contains progenitors that express markers indicative of HE and hematopoietic development including CD31, CD34, CD45, C-KIT, SCL, C-MYB, GATA2 and GATA3 (Labastie et al., 1998; Marshall et al., 1999; Oberlin et al., 2002; Tavian et al., 2001) and by gestational day 32 have in vivo multilineage repopulating capacity (Ivanovs et al., 2012).

Definitive hematopoiesis is preceded by an earlier, yolk sac (YS) restricted program, known as primitive hematopoiesis, that is characterized by the production of primitive erythrocytes, macrophages and megakaryocytes (reviewed in (Palis et al., 2010). Most evidence indicates that primitive hematopoiesis is restricted in potential and does not have the capacity to generate HSCs or lymphoid cells, but recent studies have shown that the YS can generate lymphoid progenitors prior to or in the absence of circulation (Rhodes et al., 2008; Yoshimoto et al., 2011; Yoshimoto et al., 2012). Further characterization of these yolk sac populations however, revealed that the lymphoid cells developed from a VE-cad$^+$CD41$^-$ HE-like progenitor, distinct from the VE-cad$^-$ CD41$^+$ primitive hematopoietic progenitors (Yoshimoto et al., 2011; Yoshimoto et al., 2012). These findings indicate that the YS displays both primitive and definitive hematopoietic potential and that the two populations develop from distinct progenitors.

Most studies to-date support the interpretation that lineage development from PSCs recapitulates lineage commitment in the embryo (Murry and Keller, 2008). Thus, the generation of HSCs from PSCs will depend on establishing culture conditions that not only promote HE development, but also on methods to identify these progenitors as they are specified. In an earlier study, we used T cell potential to map the onset of definitive hematopoiesis in mouse ESC differentiation cultures, and demonstrated that this program initiates from a Flk-1$^+$ Sox17$^+$ progenitor that emerged 48 hours following the onset of primitive hematopoiesis (Irion et al., 2010). Several studies have demonstrated that it is possible to generate T lymphocytes from hESCs (Galic et al., 2006; Timmermans et al., 2009).

SUMMARY OF THE INVENTION

There is described herein, use of T-cell potential to map the onset of the definitive hematopoietic program from hESCs and hiPSCs induced with specific morphogens in serum-free cultures.

In an embodiment, a candidate definitive hematopoietic progenitor population was identified that emerges between days 6 and 9 of culture, expresses surface markers and genes indicative of HE/definitive hematopoietic progenitors, and displays T-cell potential following culture on OP9-DL4 stromal cells. In addition to T-cell progenitors, this population also gives rise to erythroid and myeloid progenitors following co-culture with stromal cells. The characteristics of this population suggest that it may represent the in vitro equivalent of the human P-Sp-derived definitive hematopoietic program and as such, progenitors of human HSCs.

In an aspect, there is provided a method of enriching a population of stem cells for hematopoietic progenitors, the method comprising: inducing hematopoietic differentiation in a population of human embryonic stem cells or human induced pluripotent stem cells; sorting the population based on expression of CD43 and at least one of CD34, CD31 and CD144; and selecting a fraction that is at least one of CD34$^+$CD43$^-$, CD31$^+$CD43$^-$ and CD144$^+$CD43$^-$.

In a further aspect, there is provided a population of hematopoietic progenitors obtained using the method described herein.

In a further aspect, there is provided a method of enriching a population of stem cells for hematopoietic progenitors, comprising inhibiting activin/nodal signaling during hematopoietic differentiation. In an embodiment, the inhibiting of activin/nodal signaling comprises culturing the population with an activin/nodal inhibitor, preferably SB-431542.

In a further aspect, there is provided a use of an activin/nodal inhibitor for enriching a population of stem cells, undergoing hematopoietic differentiation, for hematopoietic progenitors. In an embodiment, the activin/nodal inhibitor is SB-431542.

BRIEF DESCRIPTION OF FIGURES

These and other features of the preferred embodiments of the invention will become more apparent in the following detailed description in which reference is made to the appended drawings wherein.

Figure 7:
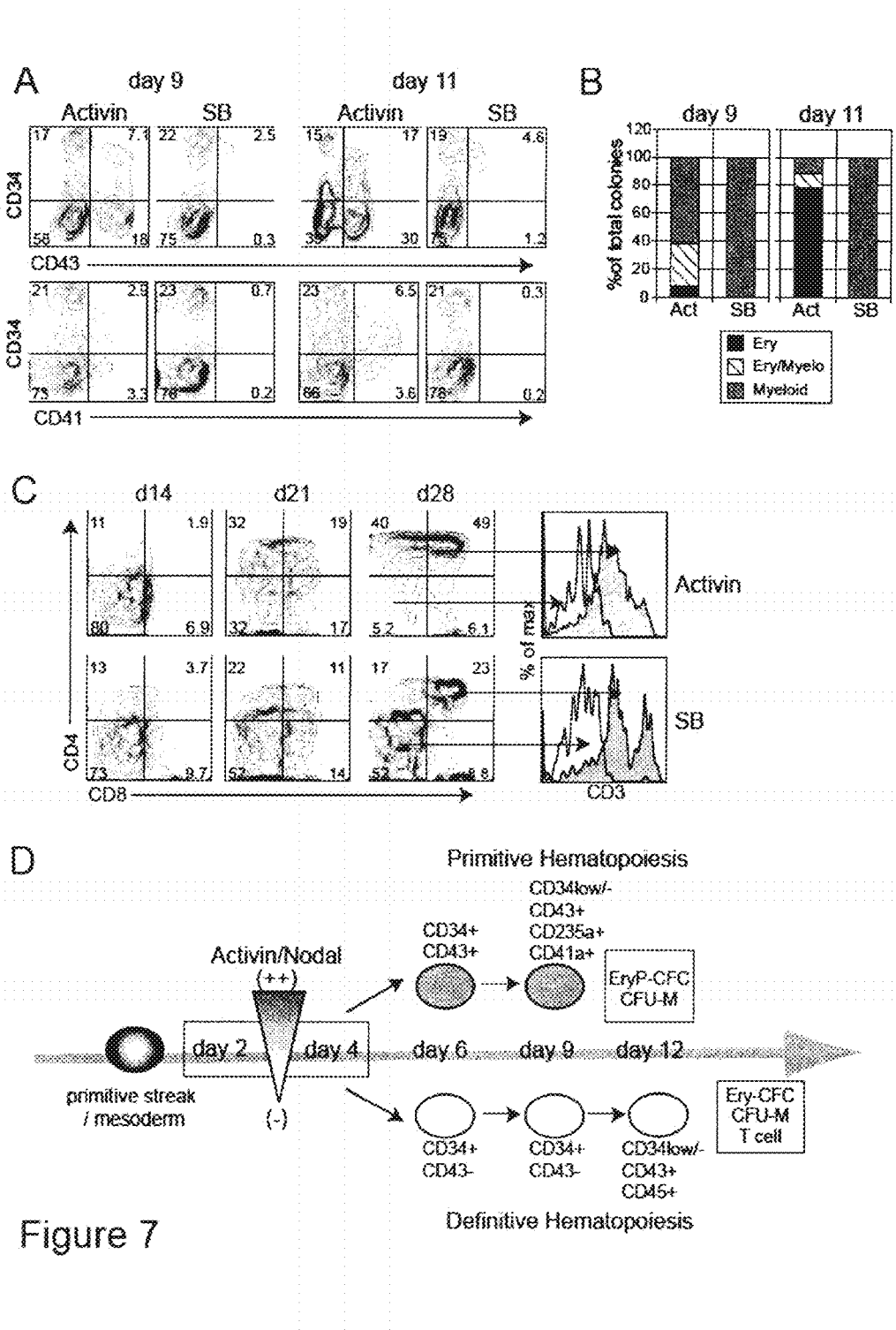

FIG. 7 shows hematopoietic potential of hiPSC-derived CD34/CD43 populations. (A) Flow cytometric analyses of hiPSC-derived SB-treated and Activin A-induced $CD34^+$ populations. (B) Progenitor potential of the 2 hiPSC $CD34^+$ populations at days 9 and 11 of differentiation. (C) Flow cytometric analyses of SB-treated and Activin A-induced populations showing emergence of $CD4^+$ and $CD8^+$ cells at indicated times. At day 28, the $CD8^+CD4^+$ populations co-expressed CD3. (D) Model showing emergence of primitive and definitive hematopoiesis in hESC differentiation cultures. Primitive hematopoiesis is dependent on Activin/nodal signaling between days 2 and 4 of differentiation and develops from a $CD34^+CD43^+$ progenitor at day 6 of differentiation. The primitive hematopoietic program develops as a $CD43^+CD41a^+CD235a^+$ population that can be detected by day 9 of differentiation. Definitive hematopoiesis is not dependent on Activin/nodal signaling between days 2 and 4 of differentiation, is specified as early as day 6 but does not expand until day 12, at which stage it is detected as a $CD43^+CD45^+$ population that does not express CD41a and CD235a.

Figure 8:
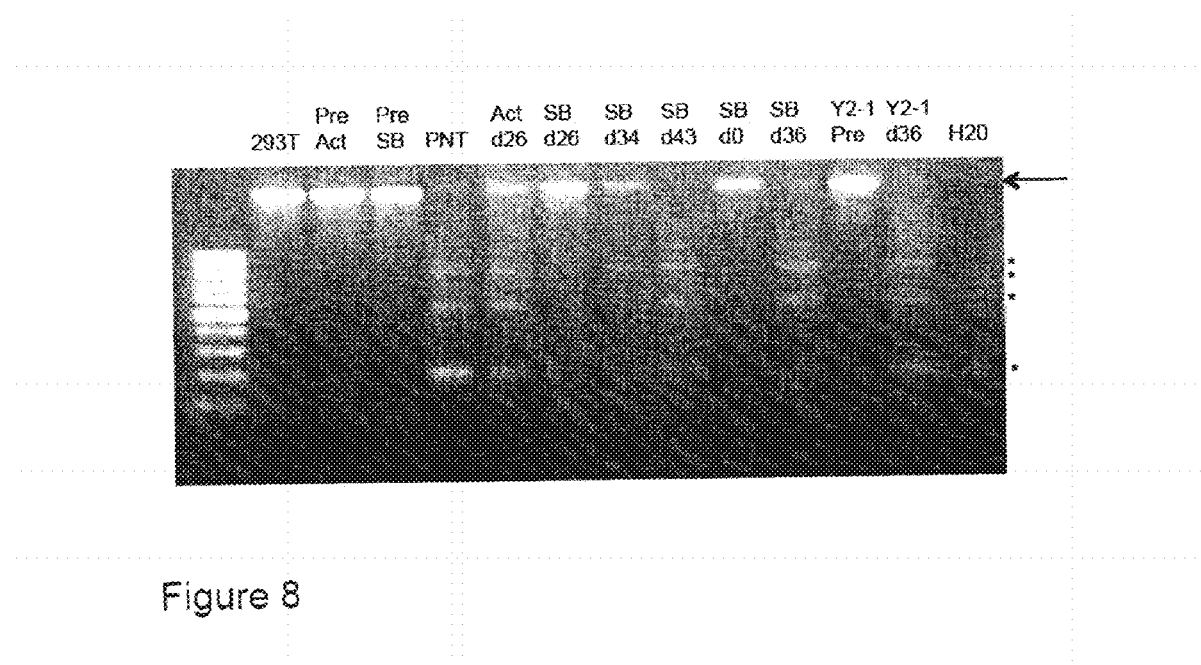

FIG. 8 shows TCR Dβ2-Jβ2 rearrangement in PSC-derived T cell populations. PCR-based analysis showing TCR Dβ2-Jβ2 rearrangement in hESC and iPSC derived T cell populations. Human post-natal thymus and 293T fibroblasts were used as rearranged and unrearranged germline controls, respectively. Arrowhead—germline PCR product. Asterisk—PCR product arising from TCR rearrangement.

Figure 9:
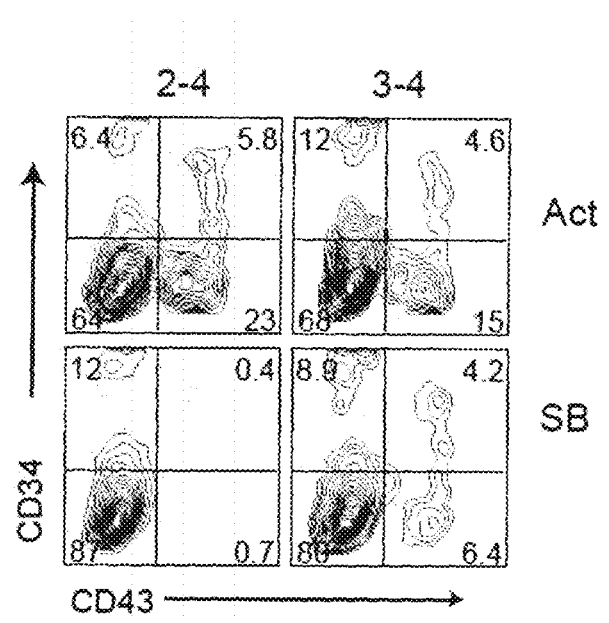

FIG. 9 shows hematopoietic potential of CD34+ progenitors. Flow cytometric analysis of CD34 and CD43 expression on day 9 EBs treated with Activin A or SB at either day 2 or day 3 of induction.

Figure 10:
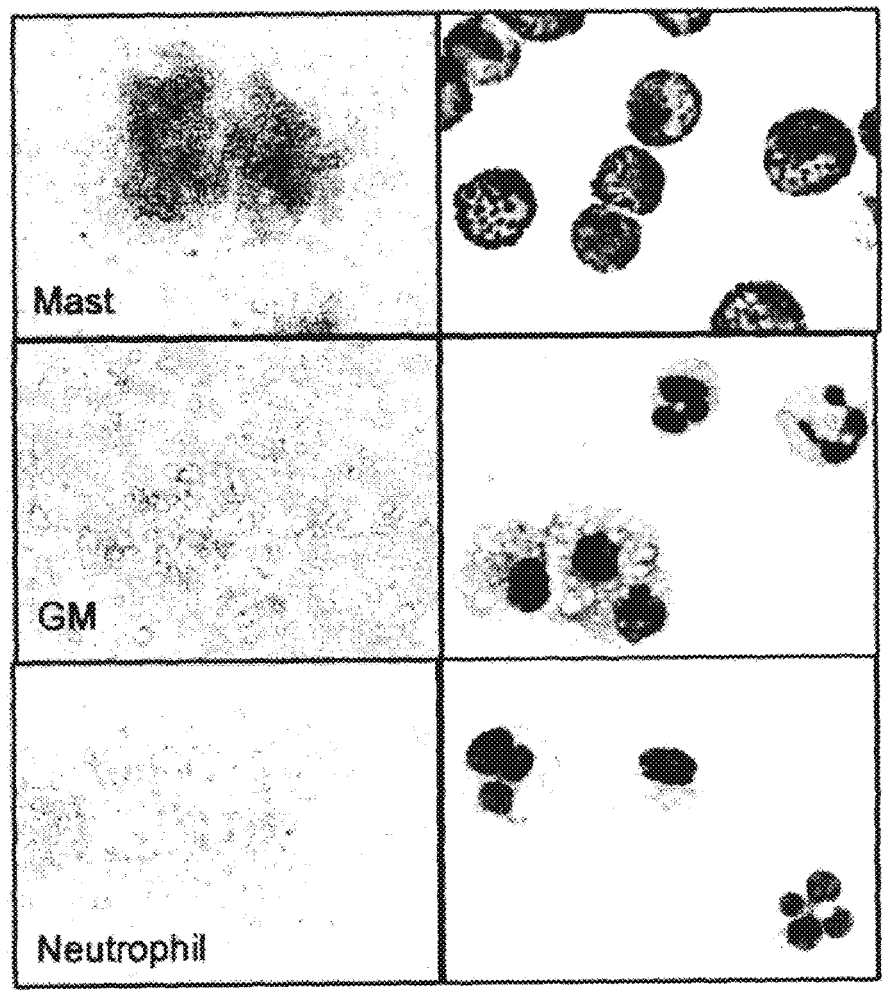

FIG. 10 shows myeloid potential of the SB-treated CD34+ population following OP9-DL 1 coculture. Photograph showing different types of myeloid colonies generated from SB-treated CD34+ cells following 7 day of co-culture on OP9-DL1 cells. Mast: colonies consisting of cells with basophilic granules, GM: colonies consisting of macrophages and neutrophils, Neutrophil: colonies consisting of neutrophils. Original magnification: colonies×100, cells× 1000.

DETAILED DESCRIPTION

The efficient generation of hematopoietic stem cells from human pluripotent stem cells (PSCs) is dependent on the appropriate specification of the definitive hematopoietic program during differentiation. We used T-lymphocyte potential to track the onset of definitive hematopoiesis from human embryonic and induced PSCs induced with specific morphogens in serum- and stromal-free cultures. We show that this program develops from a progenitor population with characteristics of hemogenic endothelium including the expression of CD34, VE-cadherin, GATA2, LMO2 and RUNX1. Along with T cells, these progenitors display the capacity to generate myeloid and erythroid cells. Manipulation of Activin/nodal signaling during early stages of differentiation revealed that development of the definitive hematopoietic progenitor population is not dependent on this pathway, distinguishing it from primitive hematopoiesis. Collectively, these findings demonstrate that it is possible to generate T-lymphoid progenitors from PSCs and that this lineage develops from a population whose emergence marks the onset of human definitive hematopoiesis.

In an aspect, there is provided a method of enriching a population of stem cells for hematopoietic progenitors, the method comprising: inducing hematopoietic differentiation in a population of human embryonic stem cells or human induced pluripotent stem cells; sorting the population based on expression of CD43 and at least one of CD34, CD31 and CD144; and selecting a fraction that is at least one of $CD34^+CD43^-$, $CD31^+CD43^-$ and $CD144^+CD43^-$. In some embodiments, the sorting is performed between about day 6 and about day 13. In some embodiments, the sorting is performed about day 10.

As used herein, "stem cell" refers to a cell that can divide (through mitosis) and differentiate into diverse specialized cell types and can self-renew to produce more stem cells. Stem cells include, without limitation, stem cells that are totipotent, pluripotent, multipotent, oligopotent and/or unipotent.

The term "enriching", as used in the context of the present invention, includes any isolation or sorting process that increases the relative abundance of a desired cell type, or cell types, in a population of cells. In an embodiment, enriched populations of cells are at least 10%, 20%, 30%, 40%, 50%, 60%, 70%, 80%, 90% or 100% of the desired cell type.

As used herein, "embryonic stem cell" or "ES cells" are pluripotent stem cells derived from the inner cell mass of the blastocyst, an early-stage embryo. ES cells are pluripotent, that is, without limitation, they are able to differentiate into all derivatives of the three primary germ layers: ectoderm, endoderm, and mesoderm. These include each of the more than 220 cell types in the adult body. Pluripotency distinguishes embryonic stem cells from adult stem cells found in adults; while embryonic stem cells can generate cells of all germ layers, adult stem cells are multipotent and can only produce a limited number of cell types. Human ES cells measure approximately 14 μm while mouse ES cells are closer to 8 μm. Additionally, under defined conditions, embryonic stem cells are capable of propagating themselves indefinitely. In some examples, embryonic stem cells are maintained as embryonic stem cell lines.

As used herein, "induced pluripotent stem cell" refers to any pluripotent stem cell artificially derived from a non-pluripotent cell, typically an adult somatic cell, by inducing a "forced" expression of specific genes.

As used herein "hematopoietic stem cell" and/or "hematopoietic progenitor cell" refers to a cell capable of developing into any mature myeloid and/or lymphoid cell. Hematopoietic stem cells may be derived from bone marrow, liver, spleen, mobilized peripheral blood or cord blood.

Methods of inducing hematopoietic differentiation in a population of human embryonic stem cells or human induced pluripotent stem cells are known to a person skilled in the art, for example, as described in 1) Kennedy, M., D'Souza, S. L., Lynch-Kattman, M., Schwantz, S., and Keller, G. (2007). Development of the hemangioblast defines the onset of hematopoiesis in human ES cell differentiation cultures. Blood 109, 2679-2687; 2) Chadwick, K., Wang, L., Li, L., Menendez, P., Murdoch, B., Rouleau, A., and Bhatia, M. (2003). Cytokines and BMP-4 promote hematopoietic differentiation of human embryonic stem cells. Blood 102, 906-915; 3) Ng, E. S., Davis, R. P., Azzola, L., Stanley, E. G., and Elefanty, A. G. (2005). Forced aggregation of defined numbers of human embryonic stem cells into embryoid bodies fosters robust, reproducible hematopoietic differentiation. Blood 106, 1601-1603.); 4)

Davis, R. P., Ng, E. S., Costa, M., Mossman, A. K., Sourris, K., Elefanty, A. G., and Stanley, E. G. (2008). Targeting a GFP reporter gene to the MIXL1 locus of human embryonic stem cells identifies human primitive streak-like cells and enables isolation of primitive hematopoietic precursors. Blood 111, 1876-1884; 5) Vodyanik, M. A., Thomson, J. A., and Slukvin, I I (2006). Leukosialin (CD43) defines hematopoietic progenitors in human embryonic stem cell differentiation cultures. Blood 108, 2095-2105; 6) Yu, C., Liu, Y., Miao, Z., Yin, M., Lu, W., Lv, Y., Ding, M., and Deng, H. (2010). Retinoic acid enhances the generation of hematopoietic progenitors from human embryonic stem cell-derived hemato-vascular precursors. Blood 116, 4786-4794; and 7) Zambidis, E. T., Peault, B., Park, T. S., Bunz, F., and Civin, C. I. (2005). Hematopoietic differentiation of human embryonic stem cells progresses through sequential hematoendothelial, primitive, and definitive stages resembling human yolk sac development. Blood 106, 860-870.

As used herein "sorting" of cells refers to an operation that segregates cells into groups according to a specified criterion (including but not limited to, differential staining and marker expression) as would be known to a person skilled in the art such as, for example, sorting using FACS. Any number of methods to differentiate the specified criterion may be used, including, but not limited to marker antibodies and staining dyes.

As used herein, "expression" or "level of expression" refers to a measurable level of expression products, such as, without limitation, the level of messenger RNA transcript expressed or of a specific exon or other portion of a transcript, the level of proteins or portions thereof expressed, the number or presence of DNA polymorphisms of the biomarkers, the enzymatic or other activities of the biomarkers, and the level of specific metabolites.

In a preferable embodiment, inducing hematopoietic differentiation is conducted under serum free conditions.

In some embodiments, inducing hematopoietic differentiation is conducted under stroma free conditions.

As used herein "stroma" refers to a supporting tissue or matrix. For example, stroma may be used for expanding a population of cells. A person of skill in the art would understand the types of stroma suitable for expanding particular cell types. Examples of stroma include MS-5, OP9, S17, HS-5, AFT024, SI/SI4, M2-10B4.

In some embodiments, inducing hematopoietic differentiation comprises culturing the population with BMP4, preferably between days 0 and 4. In some embodiments, inducing hematopoietic differentiation comprises culturing the population with about 10 ng/ml BMP4.

In some embodiments, inducing hematopoietic differentiation comprises culturing the population with bFGF, preferably between days 1 and 8. In some embodiments, inducing hematopoietic differentiation comprises culturing the population with about 5 ng/ml bFGF.

In some embodiments, inducing hematopoietic differentiation comprises culturing the population with at least one of VEGF, IL-6 and IL-11; and/or combinations thereof, preferably between days 3 and 13, further preferably between days 4 and 9. In some embodiments, inducing hematopoietic differentiation comprises culturing the population with about 15 ng/ml VEGF. In some embodiments, inducing hematopoietic differentiation comprises culturing the population with about 10 ng/ml IL-6. In some embodiments, inducing hematopoietic differentiation comprises culturing the population with about 5 ng/ml IL-11.

In some embodiments, the inducing hematopoietic differentiation comprises culturing the population with at least one of SCF and EPO, preferably between days 4 and 13, further preferably between days 6 and 9. In some embodiments, inducing hematopoietic differentiation comprises culturing the population with about 50 ng/ml SCF. In some embodiments, inducing hematopoietic differentiation comprises culturing the population with about 2 U/ml EPO.

In some embodiments, inducing hematopoietic differentiation comprises culturing the population with at least one of TPO, Flt-3 and IL-3; and/or combinations thereof, preferably between days 6 and 13, further preferably between days 8 and 9. In some embodiments, inducing hematopoietic differentiation comprises culturing the population with about 30 ng/ml TPO. In some embodiments, inducing hematopoietic differentiation comprises culturing the population with about 10 ng/ml FLT-3. In some embodiments, inducing hematopoietic differentiation comprises culturing the population with about 30 ng/ml IL-3.

In some embodiments, inducing hematopoietic differentiation comprises culturing the population with up to 1 ng/ml Activin A, preferably about 0.3 ng/ml, and further preferably about 0 ng/ml.

In some embodiments, inducing hematopoietic differentiation comprises inhibiting activin/nodal signaling. In a preferable embodiment, inhibiting activin/nodal signaling comprises culturing the population with an activin/nodal inhibitor, preferably SB-431542. In some embodiments, activin/nodal signaling is inhibited with about 6 µM SB-431542. In another embodiment, "Lefty" is used to inhibit nodal. In some embodiments, the inhibitor is added to the culture of cells between days 1.5 and 5, or between days 2 and 4 of differentiation, or about day 1.75.

"Lefty" refers to protein members of the TGF-beta family of growth factors; e.g. Lefty1 and Lefty2.

Other inhibitors of TGF-beta signaling pathway are known in the art, for example and without limitation, TGF-beta RI inhibitors SD 208, D 4476, SB 505124, GW 788388 and SJN 2511 and Activin A inhibitor Follistatin.

In some embodiments, the sorting is performed between about day 6 and about day 13, preferably between about day 7 and about day 10 of differentiation.

In some embodiments, the population is sorted based on expression of CD43 and CD34 and the selected fraction is CD34$^+$CD43$^-$.

In some embodiments, the population is sorted based on expression of CD43 and CD31 and the selected fraction is CD31$^+$CD43$^-$.

In some embodiments, the population is sorted based on expression of CD43 and CD144 and the selected fraction is CD144$^+$CD43$^-$.

In a further aspect, there is provided a population of hematopoietic progenitors obtained using the method described herein.

In a further aspect, there is provided a method of enriching a population of stem cells for hematopoietic progenitors, comprising inhibiting activin/nodal signaling during hematopoietic differentiation. In an embodiment, the inhibiting of activin/nodal signaling comprises culturing the population with an activin/nodal inhibitor, SB-431542. In some embodiments, the activin/nodal inhibitor is added to the population between about day 1 and about day 5. In some embodiments, the activin/nodal inhibitor is added to the population between about day 2 and about day 4. in some embodiments, the activin/nodal inhibitor is added to the population at about day 1.75. In some embodiments, the cells are sorted between about day 6 and about day 13. In some embodiments, the cells are sorted between about day 7 and about day 10. In some embodiments, the cells are sorted and the selected cells are CD34$^+$CD43$^-$, CD31$^+$CD43$^-$, and/or CD144$^+$CD43$^-$. In some embodiments, the population of stem cells for hematopoietic progenitors is enriched by greater than about any one of 10%, 20%, 30%, 40%, 50%, 60%, 70%, 80%, 90% and 100%.

In a further aspect, there is provided a use of an activin/nodal inhibitor for enriching a population of stem cells, undergoing hematopoietic differentiation, for hematopoietic progenitors. In an embodiment, the activin/nodal inhibitor is SB-431542. In some embodiments, the activin/nodal inhibitor is added to the population between about day 1 and about day 5. In some embodiments, the activin/nodal inhibitor is added to the population between about day 2 and about day 4. in some embodiments, the activin/nodal inhibitor is added to the population at about day 1.75. In some embodiments, the cells are sorted between about day 6 and about day 13. In some embodiments, the cells are sorted between about day 7 and about day 10. In some embodiments, the cells are sorted and the selected cells are CD34$^+$CD43$^-$, CD31$^+$CD43$^-$, and/or CD144$^+$CD43$^-$. In some embodiments, the population of stem cells for hematopoietic progenitors is enriched by greater than about any one of 10%, 20%, 30%, 40%, 50%, 60%, 70%, 80%, 90% and 100%.

In an embodiment, the population is cultured with between 1 μM to 10 mM, 1 μM to 1 mM of the activin/nodal inhibitor, or about 6 μM.

The advantages of the present invention are further illustrated by the following examples. The examples and their particular details set forth herein are presented for illustration only and should not be construed as a limitation on the claims of the present invention.

EXAMPLES

Materials and Methods
Maintenance and Differentiation of Human ES and iPS Cells

The hESC line H1 (Thomson et al., 1998) and the reprogrammed human iPS cell line (MSC-iPS1; (Park et al., 2008)) were used in this study. They were maintained on irradiated mouse embryonic fibroblasts in hESC media as described previously (Kennedy et al., 2007). Prior to differentiation, the cells were feeder-depleted by culturing on matrigel (BD Biosciences, Bedford, Mass.) in hESC media for 24 to 48 hours. To generate EBs, hPSCs were treated with collagenase B (1 mg/ml; Roche, Indianapolis, Ind.) for 20 minutes followed by a short trypsin-EDTA (0.05%) step. Cells were gently scraped with a cell scraper to form small aggregates (10-20 cells). Aggregates were resuspended in StemPro-34 (Invitrogen), supplemented with penicillin/streptomycin (10 ng/mL), L-glutamine (2 mM), ascorbic acid (1 mM), monothioglycerol (MTG, $4 \times 10^{-4}$M; Sigma), and transferrin (150 μg/mL). BMP-4 (10 ng/mL), bFGF (5 ng/mL), Activin A, 6 μM SB-431542, VEGF (15 ng/mL), Dkk (150 ng/mL), IL-6 (10 ng/mL), IGF-1 (25 ng/mL), IL-11 (5 ng/mL), SCF (50 ng/mL), EPO (2 U/mL final), TPO (30 ng/mL), IL-3 (30 ng/mL) and Flt-3L (10 ng/mL) were added as indicated. Cultures were maintained in a 5% $CO_2$/5% $O_2$/90% $N_2$ environment for the first 8 days and then transferred to a 5% $CO_2$/air environment. All recombinant factors are human and were purchased from R&D Systems (Minneapolis, Minn.).

OP9-DL4 Co-Culture for T-Lineage Differentiation

OP9 cells retrovirally-transduced to express Delta-like 4 (OP9-DL4) were generated and maintained in α-MEM medium supplemented with penicillin/streptomycin and 20% FBS (OP9 media) as previously described (La Motte-Mohs et al., 2005; Schmitt et al., 2004). 5-10×10$^4$ sorted human EB-derived subsets were added to individual wells of a 6-well plate containing OP9-DL4 cells, and cultured in OP9-media supplemented with rhFlt-3L (5 ng/mL) and rhIL-7 (5 ng/mL), (Peprotech, Rocky Hill, N.J.). rhSCF (100 ng/mL) was added for the first 8 days only. Every five days co-cultures were transferred onto fresh OP9-DL4 cells by vigorous pipetting and passaging through a 40 μm cell strainer to remove stromal cells.

OP9-DL1 Co-Culture for Erythroid/Myeloid Differentiation

Sorted cells were cultured at a concentration of 2×10$^4$ cells per well on irradiated OP9-DL1 monolayers in OP9 media with VEGF (5 ng/mL), TPO (30 ng/mL), SCF (50 ng/mL), Flt3 (10 ng/mL), IL-11 (5 ng/mL), and BMP-4 (10 ng/mL) in 24-well plates for 7 days. Cells were harvested as above.

Reaggregation Assay

Sorted populations were resuspended in day 6 media (FIG. 1A) at 25×10$^4$ cells/mL and 50 uL added to a well in a low-cluster 96-well plate. The following day, 2 wells/condition were pooled and transferred into a low-cluster 24-well plate with the addition of 1 mL of media. 24 h later, day 8 media was added to the wells and moved to normoxic conditions.

T Cell Activation

SB-treated CD34$^{++}$CD43$^-$ cells were cocultured on OP9-DL4 cells for 37-40 days. At the time of stimulation, cocultures were seeded onto fresh OP9-DL4 cells in individual wells of a 12-well plate. All wells received OP9 media supplemented with 2 ng/mL rhIL-7 and rhIL-2 and stimulated wells received the addition of 5 μg/mL α-CD3 (clone HIT3a) and 1 μg/mL α-CD28 (clone 28.2) mAbs. After 4 days, flow cytometry was performed.

Flow Cytometry and Cell Sorting

The following antibodies were used for these studies: CD3-APC (clone UCHT1), CD4-APC-EFluor750 (clone RPA-T4), CD5-PE-Cy7 (clone L17F12), CD7-FITC (clone M-T701), CD8-eFluor-650 NC (clone RPA-T8), CD31-FITC (clone WM59), CD33-FITC (clone HIM 3-4), CD34-APC (clone 8G12), CD34-PE-CY7 (clone 4H11), CD41-APC (clone HIP8), CD42b-PE (clone HIP1), CD43-PE (clone 1G10), CD45-APC-eFluor750 (clone 2D1) or CD45-PacificBlue (clone H130), CD56-PE-Cy7 (clone B159), CD90-APC (clone 5E10), CD117-APC (clone 104D2), CD144-PE (clone 123413), KDR-PE (clone 89106), TCRγδ-FITC (clone 11F2), TCRαβ-PE (clone T10B9.1A-31). Stained cells were analyzed using an LSRII (BD Biosciences) flow cytometer at the indicated time points. Data analysis was performed using FlowJo software. For T lymphoid studies, analyses were carried out by gating on live cells and lack of 6-Diamidino-2-phenylindole (DAPI) uptake, followed by gating on cells expressing CD45. All antibodies were purchased from BD Biosciences (San Diego, Calif.) with the following exceptions: CD8 eFluor-650 NC and CD34-PE-CY7 were purchased from eBioscience (San Diego, Calif.) and KDR was purchased from R&D systems. Cells were sorted with FACSAria™II (BD) cell sorter at the Sick Kids/UHN Flow Cytometry Facility.

T Lymphoid Precursor Frequency Analysis

Limiting dilution assays (LDA) of CD34+CD43− cells isolated from either Activin A induced or SB-treated EBs were performed by serial dilutions. CD34+CD43− were sorted from the EB population using the FACS Aria cell sorter, and 10000 (n=22), 3000 (n=54), 1000 (n=57), 300 (n=84) or 100 (n=90) cells of the Activin A treated subset or 10000 (n=21), 3000 (n=54), 1000 (n=60), 300 (n=83), 100 (n=114) or 30 (n=48) cells of the SB-treated subset were deposited into individual wells of a 96 well plate containing OP9-DL4 cells. Progenitors were cultured for 16 days prior to harvesting and flow cytometric analysis. The presence of CD45+CD7+CD43+CD5+ cells was scored. Progenitor frequencies were determined by the method of maximum likelihood applied to the Poisson model (Groth, 1982).

Hematopoietic Colony Assay

Analysis of hematopoietic colony potential was performed by plating either 5×103-2.5×104 sorted cells or 2.5×104-5.0×104 unfractionated EB populations in 1% methylcellulose containing specific cytokines as described in detail previously (Kennedy et al., 2007). Colonies consisting of erythroid, erythroid/myeloid and myeloid (either macrophage or mast cell) cells were quantified after 10-14 days.

Quantitative Real-time PCR

Total RNA was prepared with the RNAqueous RNA Isolation Kit (Ambion) and treated with RNase-free DNase (Qiagen). 100 ng to 1 ug RNA was transcribed into cDNA using random hexamers and Oligo (dT) with Superscript III Reverse Transcriptase (Invitrogen). Real-time quantitative PCR was performed on a MasterCycler EP RealPlex (Eppendorf). All experiments were carried out in triplicate using SYBR Green JumpStart Taq ReadyMix (Sigma). The oligonucleotide sequences are available upon request. Gene expression was evaluated as DeltaCt relative to control (ACTB).

Western Blot

Thirty minutes after the addition of DMSO, Activin A, and/or SB at day 2 of differentiation, wells were harvested and lysed on ice using RIPA buffer. Proteins were separated by SDS-PAGE, transferred onto nitrocellulose membranes and probed overnight with Smad2 (Cell Signaling, 1:1000) and phospho-Smad2 antibodies (Millipore, 1:1000, Ser 465/467). Membranes were scanned using the LI-COR Biosciences Odyssey imaging system.

PCR Analysis of T Cell Receptor Rearrangements

Genomic DNA was isolated from Activin A or SB-treated CD34+CD43−/OP9-DL4 co-cultures using the Qiagen DNeasy Blood and Tissue kit. Genomic DNA (200 ng) was amplified by polymerase chain reaction (PCR) for 30 cycles (1 min at 95° C.; 2 min at 66° C.; and 5 min at 72° C.) in 25 µL reaction buffer containing 1.5 mM MgCl2, 1 U Taq Polymerase, 10 mM dNTPs, and 400 nM each of previously published primers (Timmermans et al., 2009), detecting Dβ2-Jβ2 T cell receptor gene rearrangements. PCR products were separated using agarose gel electrophoresis with 293T fibroblasts and human post-natal thymocytes (PNT) used as germline and rearranged controls, respectively.

Results and Discussion

Serum-Free and Stroma-Free Hematopoietic Differentiation of hESCs

Figure 1:
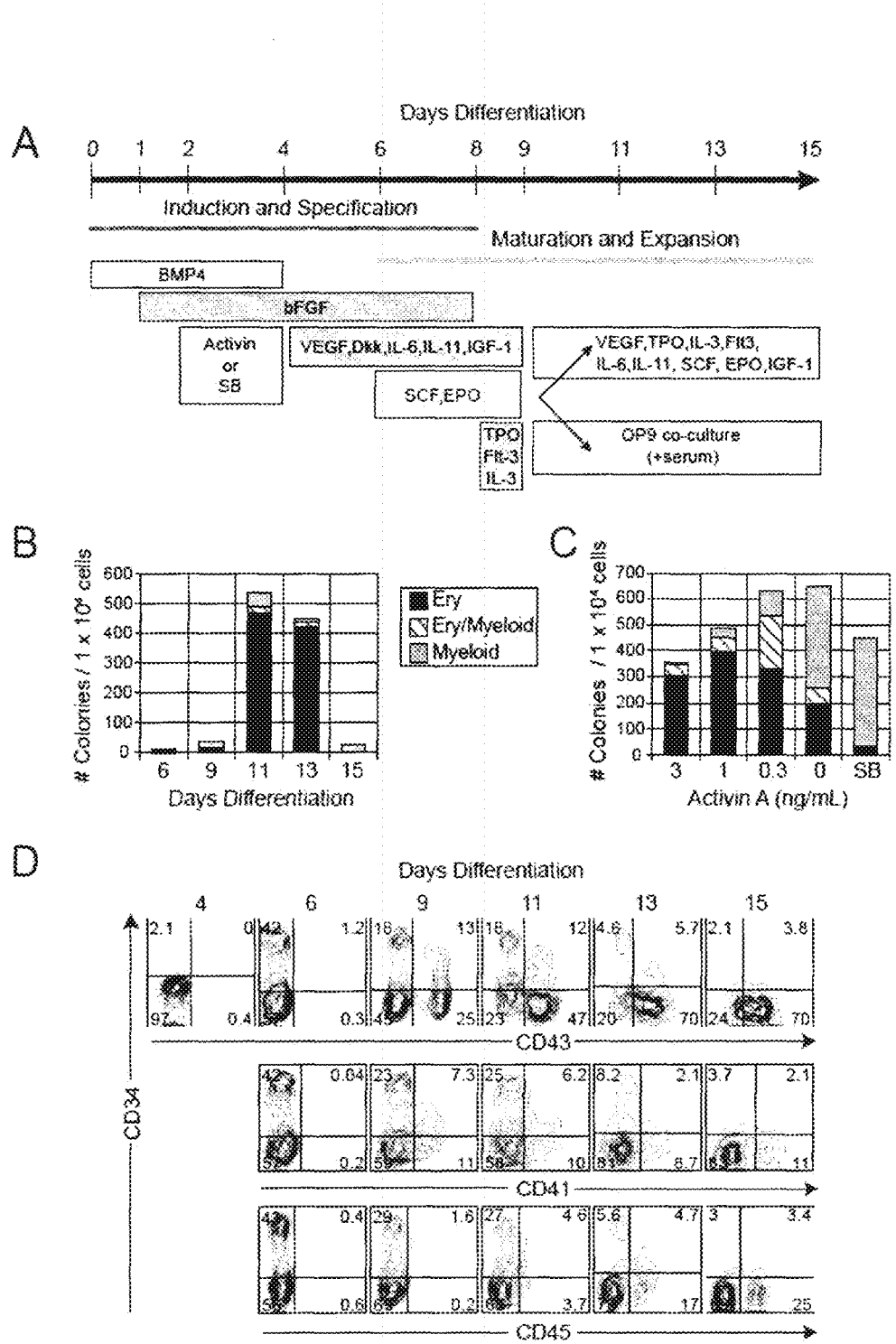
FIG. 1 shows hematopoietic induction of hESCs with Activin A and BMP4. (A) Differentiation scheme used for hematopoietic induction of human pluripotent stem cells. EBs were generated during the first 24 hours of culture in the presence of BMP-4, subsequently cultured in the presence of BMP-4 and bFGF for the next 24 hours and then in the presence of BMP4, bFGF and Activin A for the following 48 hours (days 2-4). For some experiments SB-431542 (SB) was added in place of Activin A. At day 4, BMP4 and Activin A (or SB) were removed and replaced with VEGF, IL-6, IL-11, IGF-1, SCF, EPO, TPO, Flt-3, IL-3 and DKK1 as indicated. (B) Frequency of hematopoietic progenitors detected in EBs over time. Ery: erythroid colonies; Ery/Myeloid: colonies consisting erythrocytes and low numbers of myeloid cells; and Myeloid: colonies consisting of either macrophages or mast cells. (C) Effect of Activin A stimulation or inhibition on hematopoietic progenitor development in day 13 EBs. (D) Flow cytometric analyses of CD34, CD43, CD41 and CD45 expression on the indicated days in EBs treated with 0.3 ng/ml Activin A plus the cytokines shown in (A).

To generate progenitors of the definitive hematopoietic program under serum- and stroma-free conditions, we induced the differentiation of H1 hESCs as embryoid bodies (EBs) in chemically defined media with an optimized, stage-specific combination of BMP-4, Activin A, bFGF and VEGF together with hematopoietic cytokines (FIG. 1A). With this induction scheme, colony-forming cells were detected as early as day 6 of differentiation. Their number increased modestly over the next 3 days and then dramatically by day 11 of differentiation before declining to low levels by day 15 (FIG. 1B). Most of the progenitors detected at these stages were erythroid restricted, although low numbers of both multipotential erythroid-myeloid and myeloid colony-forming cells were also present. The predominance of erythroid progenitors and their transient pattern of development suggest that this early hematopoietic population may represent human primitive hematopoiesis.

As Activin/nodal signaling is required for primitive hematopoietic development in mESC cultures (Nostro et al., 2008; Pearson et al., 2008), we next varied the Activin A concentration to determine if this pathway impacts hESC-derived hematopoiesis (FIG. 1C). Increasing concentrations of Activin A led to a reduction in myeloid progenitors and an increase in erythroid progenitors detected in day 13 EBs. In contrast, inhibition of the pathway by addition of the Activin/nodal inhibitor SB-431542 (SB; (Inman et al., 2002)) eliminated almost all erythroid progenitors (FIG. 1C). These observations indicate that the development of this early erythroid progenitor population is influenced by the levels of Activin/nodal signaling between days 2 and 4 of differentiation. Given that 0.3 ng/mL Activin A effectively induced both myeloid and erythroid progenitors, we used this concentration for the subsequent studies, unless otherwise indicated.

EBs were assayed at defined timepoints for the expression of CD34, CD43, CD41 and CD45, cell surface markers previously shown to be expressed on the earliest hematopoietic cells that develop in hESC-differentiation cultures (Vodyanik et al., 2006). A substantial population of $CD34^+$ cells was detected by day 6 of differentiation. This population steadily declined in size over the following 9 days and was no longer detectable by day 15 (FIG. 1D). $CD43^+$ cells emerged by day 9, at which time the CD34 and CD43 expression pattern was similar to that reported by others (Timmermans et al., 2009; Vodyanik et al., 2006). The $CD34^+CD43^+$ population declined over time, while the $CD34^-CD43^+$ population increased. $CD41^+$ cells were present by day 9 of differentiation, whereas $CD45^+$ cells were not detected at significant levels until day 13.

Hematopoietic Potential of the CD34/CD43 Populations

As the profile observed at day 9 of differentiation (FIG. 2A) most closely resembled the stage at which Timmermans et al. (2009) identified T-cell progenitors, we next analyzed the different CD34/CD43 fractions from this stage for hematopoietic potential by colony assays and surface marker expression. All erythroid, myeloid and erythroid/myeloid progenitors segregated to the $CD43^+$ fractions (FIG. 2B), confirming findings from earlier studies (Timmermans et al., 2009; Vodyanik et al., 2006). Neither P1 ($CD34^+CD43^-$) nor P5 ($CD34^-CD43^-$) contained any colony-forming cells. The majority of the erythroid colonies generated from the $CD43^+$ progenitors were small with a tight morphology, and contained large nucleated cells that expressed high levels of ε-globin and very low levels of β-globin (FIG. 6D, E), indicating that they are primitive erythroblasts.

Figure 2:
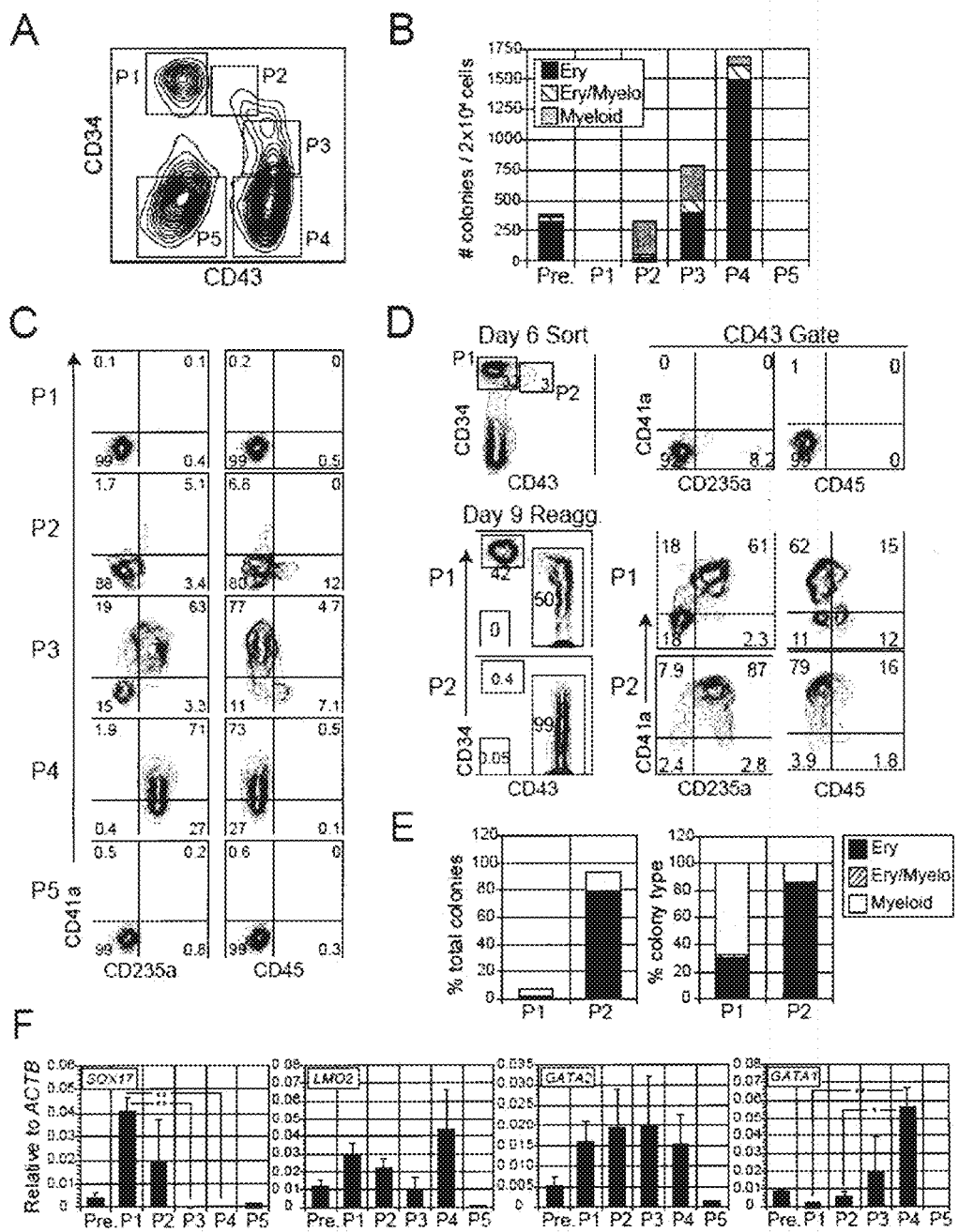
FIG. 2 shows primitive hematopoietic potential of day 9 CD34/CD43 populations. (A) Flow cytometric analyses showing the CD34 and CD43 fractions isolated from day 9 EBs; P1: 10%±3%, P2: 1.5%±0.7%, P3: 12.5%±–4%, P4: 21%±8% and P5: 35%±9% (±SD, n=5) (B) Erythroid and myeloid progenitor potential of the CD34/CD43 fractions (C) Flow cytometric analyses showing expression of CD41a, CD235a and CD45 on the fractions indicated in (A). (D) Hematopoietic potential of day 6 CD34$^+$CD43$^-$ and CD34$^+$CD43$^+$ populations. Day 6 sort (upper panels): Flow cytometric analyses showing populations isolated for hematopoietic studies. Cells were isolated, cultured for 3 days as aggregates and analyzed. Day 9 Reagg (middle and lower panels): Flow cytometric analyses showing expression of CD34, CD43, CD41a, CD235a and CD45 on populations generated from indicated sorted fractions following 3 days of culture. (E) Primitive erythroid/myeloid potential of the day 9 aggregate populations generated from the P1 and P2 day 6 fractions. Left graph indicates the proportion of total colonies generated from the entire CD34$^+$ population that were derived from the P1 and P2 fractions. Right graph shows the proportion of different types of colonies generated from the 2 different fractions. (F) RT-qPCR expression analyses of the different CD34/CD43 fractions for the indicated genes. Bars represent mean±standard deviation of the mean of samples from three independent experiments. Asterisks indicate statistical significance as determined by t-test; *($p\leq0.05$), **($p\leq1.01$).

Previous studies have shown that the co-expression of CD41a and CD235a identify an early developing population in hESC cultures that contains primitive erythroid and megakaryocyte progenitors (Klimchenko et al., 2009; Vodyanik et al., 2006). Flow cytometric analyses showed that CD41a and CD235a were broadly expressed on the $CD43^+$ P3 and P4 populations that also exclusively contained the erythroid progenitors. CD45 expression was restricted to small subsets of the P2 and P3 fractions and was never co-expressed with CD235a (FIG. 2C and data not shown). Cells in the P1 and P5 fractions did not express any of these markers. Taken together, these observations are consistent with those described previously and support the interpretation that the early expression of CD41a and CD235a marks the emergence of human primitive hematopoiesis.

The CD43⁺CD41a⁺CD235a⁺ Populations Develop from CD34⁺ Progenitors

We were next interested in determining if the primitive erythroid population generated under defined conditions is derived from a CD34⁺ intermediate as a previous study has shown that the earliest hESC-derived hematopoietic cells generated in serum induced cultures develop from a CD34⁺ progenitor (Vodyanik et al., 2006). To address this question, we analyzed progenitors at day 6 of differentiation, a stage prior to the expansion of the CD43⁺CD41a⁺CD235a⁺ primitive population. Both the CD34⁺CD43⁻ and the smaller CD34⁺CD43⁺ populations detected at this stage (FIG. 2D) were sorted, reaggregated, cultured for an additional 3 days (day 9 total) and then analyzed. The entire CD34⁺CD43⁺-derived population expressed CD43 and the majority of these cells co-expressed CD41a and CD235a (FIG. 2D, lower panel). In contrast, only 50% of the CD34⁺CD43⁻-derived population expressed CD43 and of these, approximately 60% co-expressed CD41a and CD235a (middle panel). Consistent with these differences, the CD34⁺CD43⁺ population generated 13-fold more progenitors than the CD34⁺CD43⁻ population (FIG. 2E), the majority of which were primitive erythroid. The CD34⁺CD43⁻ population gave rise to predominantly myeloid progenitors. Taken together, these data clearly demonstrate that human primitive hematopoiesis develops from a CD34⁺ progenitor that emerges as early as day 6 in the differentiation cultures and can be identified by co-expression of CD43.

Definitive Hematopoietic Potential of the CD34/CD43 Fractions

RT-qPCR analyses revealed that SOX17, which defines the emergence of definitive hematopoiesis in the mouse ESC differentiation model Orion et al., 2010) was expressed at highest levels in the P1 cells, to a lesser extent in the P2 cells and not at all in the P3 and P4 primitive populations (FIG. 2F). LMO2 and GATA2 were expressed in all populations, whereas GATA1 expression was highest in the P4-derived population that contained the highest frequency of erythroid progenitors.

Figure 3:
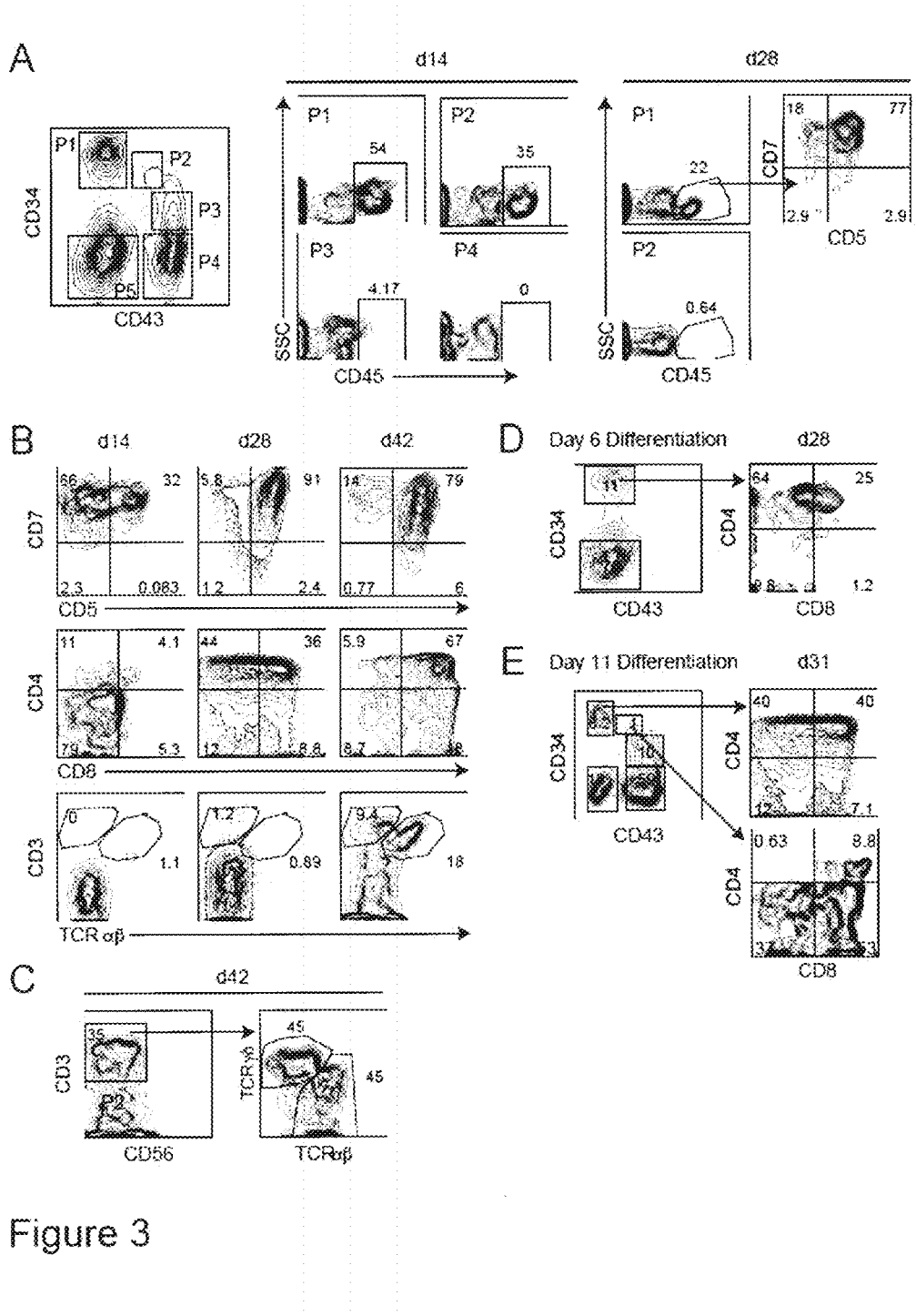
FIG. 3 shows T cell potential of the CD34/CD43 populations. (A) Flow cytometric analyses showing the proportion of CD45$^+$ cells generated from fractions P1-P4 following 14 days of co-culture on OP9-DL4 and of CD7$^+$CD5$^+$ T-lymphoid progenitors generated from fraction P1 at day 28 of co-culture. (B) Kinetics of T cell development from the CD34$^+$CD43$^-$ fraction. Cultures were harvested as indicated and analysed by flow cytometry. (C) Development of TCRαβ and TCRγδ T cells from CD34$^+$CD43$^+$ progenitors at day 42 of co-culture. (D) T cell potential of day 6 CD34$^+$CD43$^-$ progenitors. Cultures were harvested and analyzed for CD4 and CD8 expression on day 28. (E) T cell potential of CD34$^+$CD43$^-$ and CD43$^+$CD43$^{low}$ progenitors isolated from day 11 EBs. Cultures were harvested and the cells analyzed on day 31.

To further assess the definitive potential of the day 9 CD34⁺/CD43⁺ populations, each was assayed for T cell potential by co-culturing them on OP9-DL4 (Schmitt et al., 2004). T cell progenitors were only detected in P1 (FIG. 3A) consistent with the observation that these cells express the highest levels of SOX17. The P3 and P4 fractions failed to generate any CD45⁺ cells following 2 weeks of culture on OP9-DL4 stroma, whereas the P2 cells gave rise to a transient CD45⁺ population that was detectable at 2 weeks but failed to undergo T-lymphopoiesis (FIG. 3A). The P1 cells generated CD5⁺CD7⁺ T cell progenitors as early as day 14 of culture, CD4⁺CD8⁺ T cells by day 28 and CD3⁺ T cells expressing either TCRαβ⁺ or TCRγδ⁺ at day 42 (FIG. 3B,C). To further characterize the extent of T cell development, we analyzed genomic DNA from the co-cultured cells for the presence of TCR Dβ2-Jβ2 rearrangements. As shown in FIG. 8, the hESC-derived T cells contained multiple PCR products, indicative of polyclonal Dβ2-Jβ2 rearrangements. The expression patterns of early and late T-lineage differentiation markers from hESC-derived CD34⁺/OP9-DL4 cultures described here are similar to what is typically observed using cord blood-derived HSCs (Awong et al., 2009).

Temporal analyses of EB development revealed that the CD34⁺ population at day 6 of differentiation also contained progenitors with T cell potential (FIG. 3D) as did both the CD34⁺CD43⁻ and CD34⁺CD43$^{low}$ populations at day 11 (FIG. 3E). The CD34⁺CD43$^{low}$ population identified at this stage may be similar to the T progenitor population described previously (Timmermans et al., 2009). In contrast, the day 3 KDR⁺ hemangioblast population did not give rise to T cells, indicating that progenitors with lymphoid potential develop sometime between days 3 and 6 of differentiation (data not shown).

Figure 4:
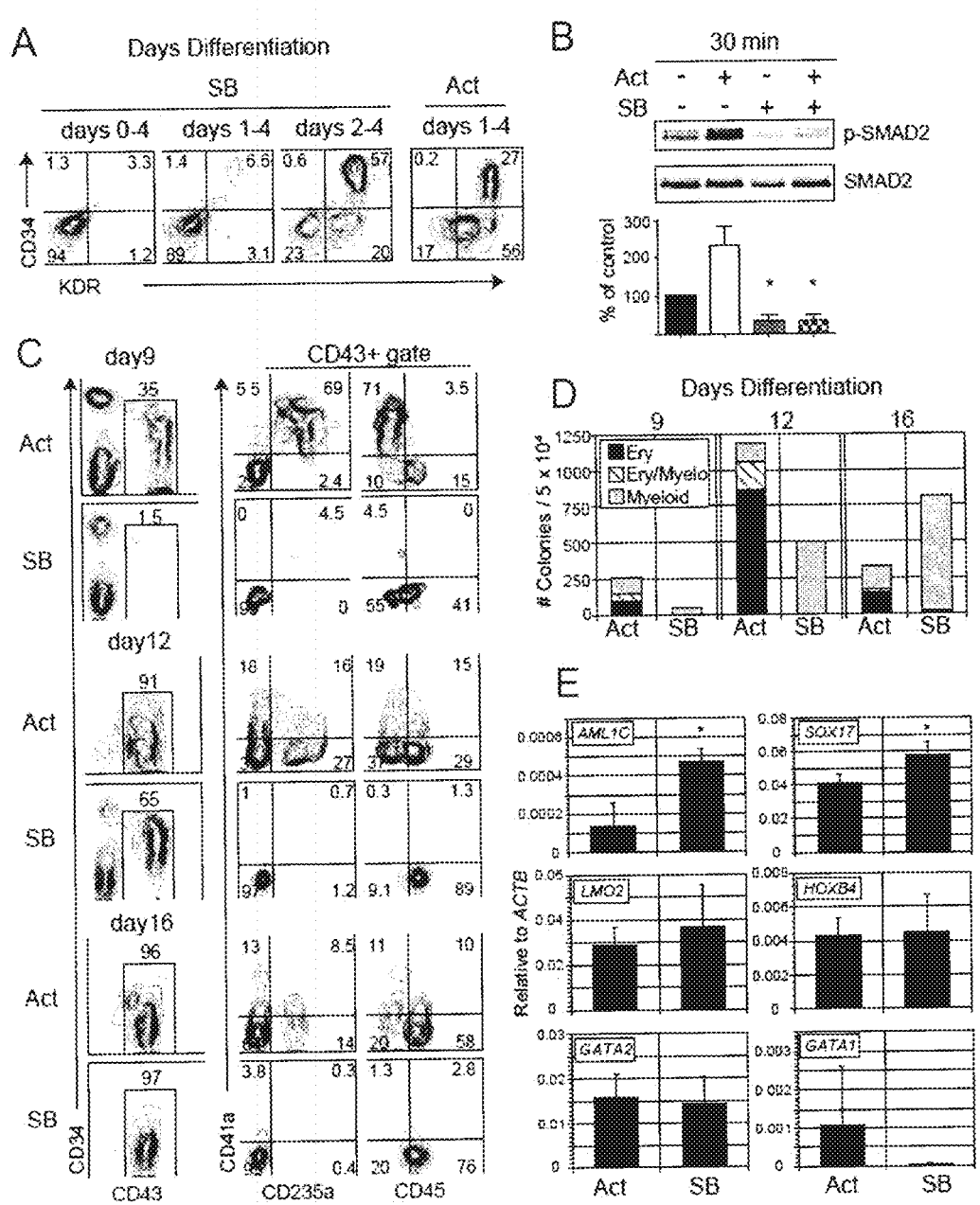
FIG. 4 shows the potential of CD34$^+$ progenitors isolated from SB-431542 treated EBs. (A) Flow cytometric analysis showing development of CD34$^+$KDR$^+$ populations at day 5 of differentiation, following addition of SB during the indicated times (SB), Act: EBs were treated with Activin A between day 1-4 of differentiation (B) Immunoblot analysis for the expression of Smad2 and phospho-Smad2 from cell lysates of EBs treated for 30 minutes at day 2 of differentiation with DMSO, Activin-A and/or SB; densitometry was performed and depicted as a graph of phospho-SMAD2 levels as % of control expression (DMSO). (C) Flow cytometric analyses showing co-expression of CD41a, CD235a and CD45 on CD43$^+$ populations in Activin A-induced and SB-treated EBs on days 9, 12 and 16 of differentiation. (D) Progenitor potential of Activin A-induced and SB-treated EBs at the indicated days of differentiation. (E) qPCR based expression analyses of CD34$^+$ fractions isolated from day 9 Activin A-induced and SB-treated EBs. Bars represent mean±standard deviation of the mean of samples from three independent experiments. Asterisks indicate statistical significance as determined by t-test; *($p\leq0.05$).

Together, the findings from these analyses demonstrate that at day 9 of differentiation, definitive hematopoietic progenitors, as defined by T cell potential, are restricted to a CD34⁺CD43⁻ population and distinct from the CD43⁺ primitive hematopoietic population The Requirement for Activin/Nodal Signaling Distinguishes Primitive and Definitive Hematopoiesis As Activin/nodal signaling is known to play a role in primitive hematopoiesis in mESC differentiation cultures (Nostro et al., 2008; Pearson et al., 2008) and our earlier findings here showed that it is required for the early wave of erythroid progenitors (FIG. 1C), we were next interested in determining if we could selectively block the development of the entire CD43⁺/CD41a⁺/CD235a⁺ population through appropriately staged inhibition of the pathway. When added within the first 24 hours of differentiation, the Activin/nodal inhibitor SB completely blocked the induction of the KDR⁺ CD34⁺ hematopoietic mesoderm population detected at day 5 of differentiation, (FIG. 4A) consistent with the known requirement of this pathway for primitive streak/mesoderm formation (Conlon et al., 1994). However, if addition of SB was delayed and added between days 2 and 4 of differentiation, KDR⁺ and CD34⁺ populations developed normally and were similar in size to those in the Activin A-induced population (FIG. 4C). Western blot analyses showed the presence of phospho-SMAD2 in the day 2 EBs, indicating that endogenous Activin/nodal signaling is active at this stage (FIG. 4B). Densitometry confirmed that the levels of phospho-SMAD2 were significantly reduced following SB treatment, indicating that SB blocked Activin/nodal signaling. Analyses of day 9 EBs revealed that inhibition of the pathway between days 2 and 4 completely blocked the development of the CD43⁺ population, but did not appear to impact the CD34⁺ cells (FIG. 4C). Complete inhibition of a CD43⁺ population at day 9 was dependent on the addition of SB at day 2 of differentiation, as delay until day 3 resulted in the development of some CD43⁺ cells (FIG. 9). A large CD43⁺ population developed from the SB-treated EBs by day 12 of culture. However, in contrast to those derived from Activin A-induced EBs, these cells did not express CD41a or CD235a, but did express CD45 (FIG. 4C). The marker profile of the SB-treated CD43⁺ population did not change between days 12 and 16 of culture. As expected at day 9 the majority of the Activin A-induced population co-expressed CD41a and CD235a.

Consistent with the absence of the CD43⁺CD41a⁺ CD235⁺ population and with our earlier observations, erythroid progenitors were not detected in the SB-treated EBs at any of the timepoints assayed here (FIG. 4D). RT-qPCR analyses revealed that the CD34⁺ population isolated from the SB-treated EBs expressed higher levels of SOX17 and AML1C than the CD34⁺CD43⁻ population generated in the Activin A-induced EBs (FIG. 4E). Levels of expression of LMO2, GATA1, GATA2, and HOXB4 were comparable in the two populations.

Figure 5:
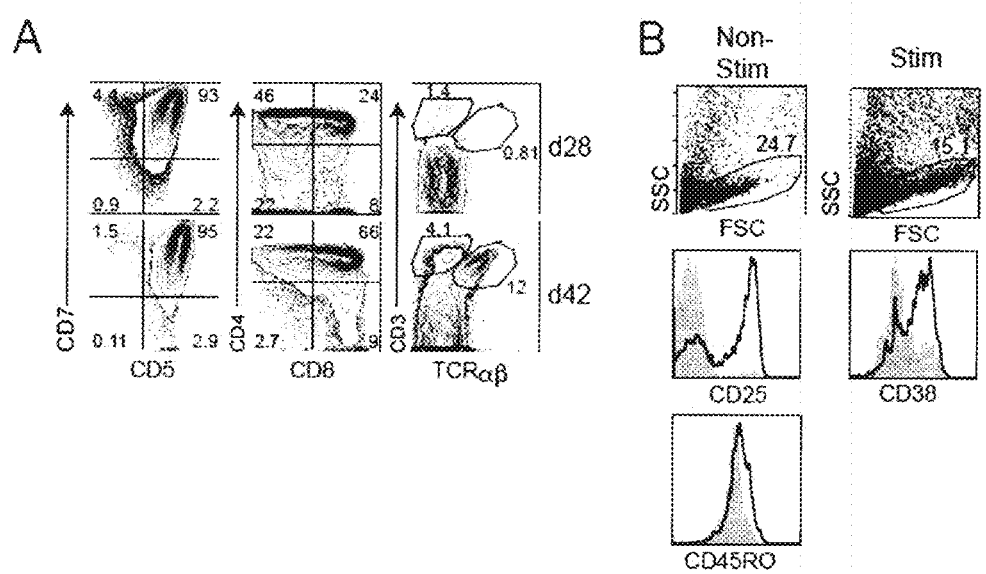
FIG. 5 shows lymphoid potential of the SB-treated CD34$^+$ population. (A) Flow cytometric analyses of SB-treated EBs showing development of CD7$^+$CD5$^+$, CD4$^+$CD8$^+$ and CD3$^+$ TCRαβ$^+$ populations at day 28 and day 42 of co-culture. (B) Functional analyses of hESC-derived T cells. Flow cytometric analyses showing forward (FSC) and side (SSC) scatter parameters and expression of CD25, CD38 and CD45RO on hESC-derived T cells following 4 days of stimulation with α-CD3 and α-CD 28 antibodies. Control cells were treated with cytokines alone.

Similar to Activin A-induced CD34⁺ cells, the SB-treated day 9 CD34⁺ progenitors generated T cells when cultured on OP9-DL4 cells (FIG. 5A). Interestingly, limiting dilution analyses revealed that the frequency of T cell progenitors in the SB-treated CD34⁺ population was more than 3-fold higher than in the Activin A-induced CD34⁺CD43⁻ population (Table 1), indicating that inhibition of the primitive hematopoietic program early in the differentiation cultures coincides with an enrichment of T cell progenitors in the day 9 CD34$^+$ population. As observed with the T cells generated from the Activin A-induced progenitors, T cells derived from the SB-treated CD34$^+$ cells also displayed polyclonal Dβ2-Jβ2 rearrangements (FIG. 8). By days 36-43 of co-culture, the majority of cells exhibited TCRβ rearrangements as shown by the loss of the germline band.

TABLE 1

Progenitor frequency analysis of Activin A or SB-treated CD34$^+$ cells

| Treatment[a] | Progenitor Frequency$^{-1}$ [95% confidence limits][b] |
|---|---|
| Activin A | 3318 [2473-4453] |
| SB | 966 [754-1237] |

[a]Sorted CD34$^{++}$ CD43$^-$ obtained from EB cultures treated with either Activin A or B were placed in limiting numbers in wells of a 96-well/plate containing OP9-DL4 cells, and cultured for 16 days before harvesting for flow cytometric analysis.
[b]Individual wells were scored for the presence of T cells based on CD45$^+$ CD43$^{+CD7++}$ CD5$^+$staining. Statistical analysis was performed via the method of maximum likelihood applied to the Poisson Model.

To determine if these T cells were functional, cells cultured for 35-40 days were stimulated for 4 days with soluble α-CD3 and α-CD28 antibodies. As shown in FIG. 5B, the stimulated CD3+ T cell showed an increase in forward scatter compared to the control cells reflecting an increase in size indicative of the early stages of activation (June et al., 1990). The α-CD3/α-CD28-induced cells also expressed significantly higher levels of CD25 and CD38 two markers classically upregulated on activated human T cells (P≤0.01) (Funaro et al., 1990; Schuh et al., 1998) Also, consistent with normal human T cell activation, an increase in the CD45RO isoform was observed on stimulated hESC-derived T cells. (FIG. 5B). These changes in the expression of activation markers show that hESC-derived T cells bear a functional T cell receptor capable of sensing and responding to stimuli. Together, with the demonstration of extensive TCR rearrangements, the presence of functional T cell receptors suggests that hESC-derived T cells are undergoing normal maturation.

Collectively, the findings from these studies demonstrate that early stage inhibition of the Activin/nodal pathway blocks primitive hematopoiesis while enhancing the T cell potential of the definitive CD34$^+$ population. They also show that the CD43$^+$ population that develops in the SB-treated EBs differs from the day 9 Activin A-induced population with respect to CD41a and CD235a expression, and as such allow us to define distinct primitive and definitive stages of CD43 development.

Hematopoietic Potential of the CD34$^+$ Population

Figure 6:
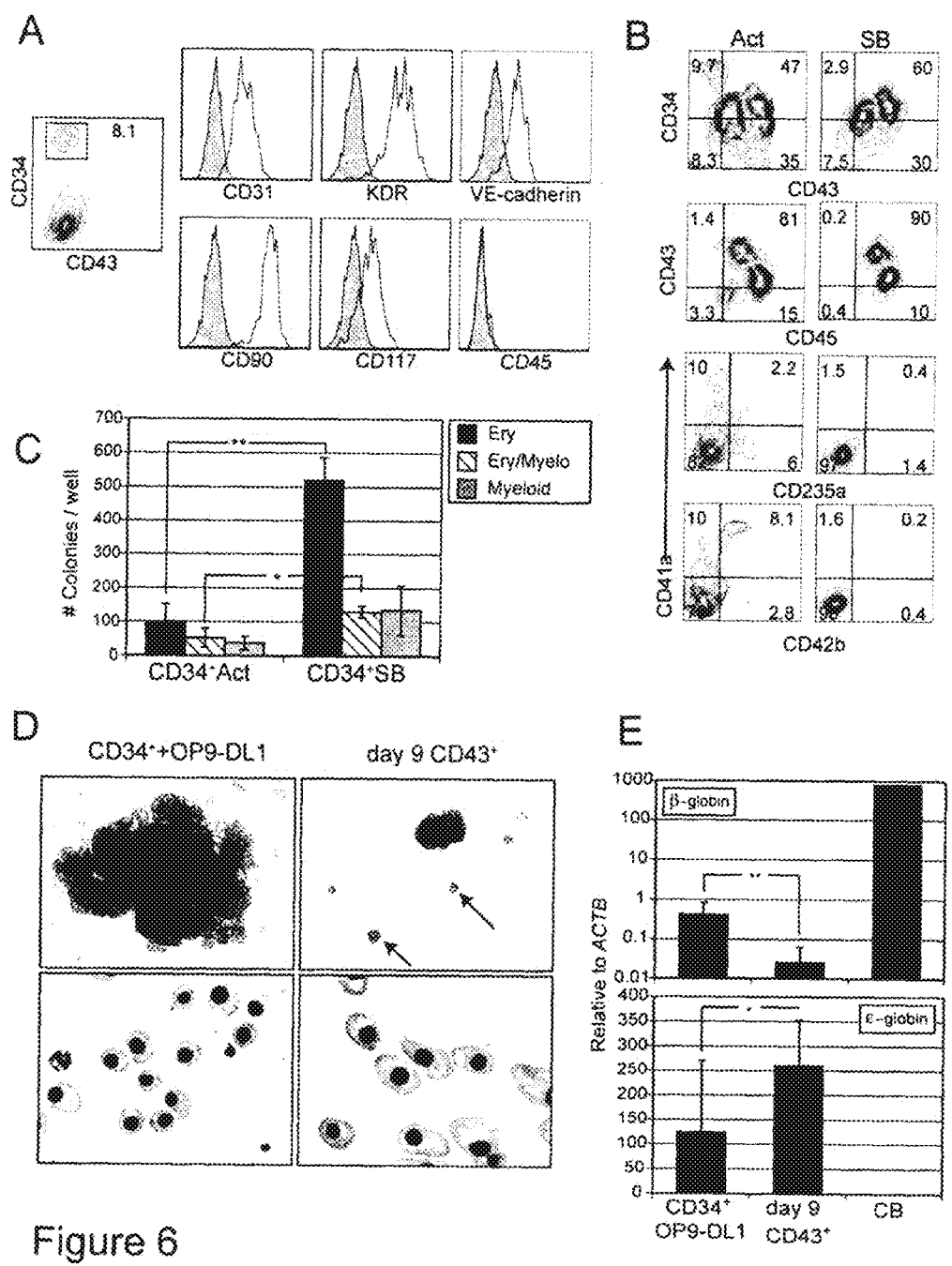
FIG. 6 shows hematopoietic potential of CD34$^+$ progenitors. (A) Flow cytometric analyses of the CD34$^+$ population from day 8 SB-treated EBs. (B) Flow cytometric analyses of SB-treated and Activin A-induced CD34$^+$ populations following 7 days of co-culture on OP9-DL1 stromal cells. Cultures were initiated with 20,000 cells of each population in a well of a 24-well plate. (C) Progenitor potential of the two CD34$^+$ populations following 7 days of co-culture. Colony numbers are calculated per well. Bars represent standard deviation of the mean of culture of a single experiment, representative of 5 independent experiments. Asterisks indicate statistical significance as determined by t-test; *($p\leq0.015$)**($p\leq0.001$). (D) Photographs showing morphology and relative size of the colonies (and the cells from them) generated from SB-treated CD34$^+$ progenitors following 7 days of co-culture and from CD43$^+$ primitive progenitors (CD43$^+$) plated directly following sorting from day 9 EB populations. Arrows indicate small, primitive erythroid-like colonies. Original magnification: colonies ×100; cells×1000. (E). RT-qPCR-analyses of β- and ε-globin expression in pools of CD34$^+$- and CD34$^-$CD43$^+$- derived erythroid colonies. Bars represent mean±standard deviation of the mean of samples from n≥7 individually isolated colonies. Asterisks indicate statistical significance as determined by t-test; *($p \leq 0.05$)**($p \leq 0.01$).

The Activin A-induced (not shown) and SB-treated definitive CD34$^+$ population co-expresses CD31, KDR and VE-CAD, markers found on HE (reviewed in (Tavian et al., 2010)), and CD90 and CD117, markers found on CD34$^+$ cord-blood derived HSCs (FIG. 6A; (Doulatov et al., 2010; Notta et al., 2011)). These populations did not, however, express CD45. To determine if the populations displayed myeloid and erythroid potential in addition to T cell potential, the cells were cultured on OP9-DL1 stromal cells in the presence of hematopoietic cytokines. OP9-DL1 cells were used rather than the wild type OP9 cells that are normally used for expansion of hematopoietic cells (Feugier et al., 2005), as we found that they supported the development of higher numbers of erythroid progenitors (not shown). Following 7 days of co-culture the Activin A-induced CD34$^+$ cells generated a CD43$^+$CD45$^+$ population, as well as a small CD41a$^+$ population. Co-expression of CD42b on some of these CD41a$^+$ cells suggests that they represent developing megakaryocytes. The SB-treated CD34$^+$ cells gave rise to a CD43$^+$CD45$^+$ population (FIG. 6B) that did not express significant levels of CD41a or CD235a.

The CD34$^+$CD43$^-$ populations also acquired erythroid and myeloid progenitor potential following 7 days of co-culture (FIG. 6C). Interestingly the SB-treated cells generated significantly higher numbers of erythroid and erythroid-myeloid progenitors than the Activin A-induced progenitors, suggesting that, in addition to T cell progenitors, this population is also enriched in erythroid/myeloid potential. The erythroid progenitors generated from the co-culture gave rise to colonies (FIG. 6D) that were substantially larger than the day 9 CD43$^+$-derived primitive erythroid colonies. Although both colony-types contained nucleated red cells (FIG. 6D, lower panels) the CD34$^+$-OP9-DL1 co-culture-derived colonies expressed significantly higher amounts of β-globin than the CD43-derived primitive colonies (FIG. 6E). The reverse pattern was observed for ε-globin expression, although the large colonies still express considerable levels of this globin. The CD34$^+$-derived myeloid population consisted of progenitors of the macrophage, mast cell and neutrophil lineages (FIG. 10). Collectively, the findings from these co-culture studies clearly demonstrate that the CD34$^+$ definitive population displays erythroid and myeloid in addition to T cell potential.

Definitive Hematopoietic Development from iPSCs

To determine if the directed differentiation approach described above can be applied to other human pluripotent stem cell lines, we induced the iPSC line MSC-iPS1 (Park et al., 2008) as in FIG. 1A. As shown in FIG. 7 (A,B), differentiation led to the development of expected CD34$^+$/CD43$^+$ and CD34$^+$/CD41$^+$ populations, as well as the spectrum of erythroid, erythroid/myeloid and myeloid progenitors. The addition of SB between days 2 to 4 inhibited the development of the CD41$^+$/CD43$^+$ populations and the erythroid and erythroid-myeloid progenitors, as observed with the hESC line. Furthermore, the CD34$^+$ cells produced by either Activin A or SB differentiation conditions generated CD4$^+$CD8$^+$ T cells that co-expressed CD3 (FIG. 7C) and displayed Dβ2-Jβ2 TCR rearrangement (FIG. 8). Taken together, these observations demonstrate that the combination of T cell development and staged manipulation of Activin/nodal signaling can be used to identify and enrich for definitive hematopoietic progenitors in hiPSC cultures and distinguish them from primitive hematopoietic progenitors.

The derivation of HSCs from hPSCs will require strategies that establish the developmental program that gives rise to this population in the early embryo. Insights from studies using different model organisms outline a developmental progression leading to the generation of HSCs that includes the induction of a definitive hematopoietic progenitor population known as HE and the subsequent specification of this population to a hematopoietic fate, giving rise to multipotent progenitors and engraftable cells. A major challenge in recapitulating embryonic hematopoiesis in PSC differentiation cultures is that the two hematopoietic programs are not spatially separate, and as a consequence the predominance of primitive hematopoiesis at early stages makes it difficult to identify the definitive hematopoietic progenitors as they develop. In this study, we used T cell potential to track the onset of definitive hematopoiesis from hPSCs, and in doing so, identified a definitive hematopoietic program that can be distinguished from the primitive hematopoietic program based on developmental potential, cell surface markers and dependency on Activin/nodal signaling.

The expression profile of the definitive CD34$^+$ population, which includes the transcription factors GATA2, LMO2, AML1C, as well as endothelial (KDR, CD31, VE-CAD), but not hematopoietic (CD45 or CD43) surface markers, suggests that it represents the equivalent of human HE. The generation of a population with these characteristics that possess T cell potential is unique and represents a critical first step in generating HSCs. Several other studies have described hESC-derived endothelial progenitor populations which, display hematopoietic potential (Choi et al., 2012; Hong et al., 2011; Wang et al., 2004; Zambidis et al., 2005). In the most recent of these reports, Choi et al (2012) identified a hemogenic endothelial progenitor (HEP) that appears to be distinct from the BL-CFC (hemangioblast), the progenitor of the primitive hematopoietic program. However as lymphoid potential was not evaluated in this or any of the other studies, it is unclear if these populations represent progenitors of the definitive hematopoietic program.

Following co-culture for 7 days on OP9-DL1 the CD34$^+$ population upregulates expression of CD43 and CD45 and acquires erythroid and myeloid progenitor potential, a transition that may represent the equivalent of the specification of HE to a hematopoietic fate. Our studies have shown that OP9-DL1 stroma is more efficient at promoting erythroid progenitor development than OP9 stroma, suggesting that Notch signaling may be required for this specification step. The CD34$^+$-derived erythroid progenitors generate large erythroid colonies that are morphologically distinct from and express significantly higher levels of β-globin than the Activin-induced CD43$^+$-derived primitive erythroid colonies. These observations combined with the fact that they develop from phenotypically and temporally different populations clearly demonstrate that these erythroid progenitors are not the same. Previous studies have described the emergence of different erythroid progenitors in serum-induced EBs over time and suggested that they represented progeny of both primitive and definitive hematopoiesis (Chadwick et al., 2003; Zambidis et al., 2005). The CD34$^+$-derived erythroid progenitors described here are distinct from the CD43$^+$-derived primitive progenitors, but they generate still express high levels of ε-globin. It is possible that the CD34$^+$-derived progenitors represent one step beyond the primitive program, a transition between primitive and definitive erythropoiesis.

With the identification of the CD34$^+$ definitive progenitors in day 9 EBs, we were able, for the first time, to define distinct human definitive and primitive hematopoietic populations (model; FIG. 7D) that display the following characteristics. First, the primitive hematopoietic population that emerges at day 9 expresses CD43 together with CD41a and CD235a whereas the definitive population that develops after day 9 expresses CD43 together with CD45, but not CD41a or CD235a. CD41a and CD235a are expressed at later stages in the definitive program where they are restricted to the megakaryocyte and erythroid lineages respectively (Andersson et al., 1981; Phillips et al., 1988). Second, development of the human primitive hematopoietic program is dependent on Activin/nodal signaling beyond day 2 of differentiation. Definitive hematopoiesis, in contrast, does not require this pathway between days 2 and 4 of differentiation. Third, both primitive and definitive hematopoiesis develop from a CD34$^+$ progenitor. Co-expression of CD43$^+$ with CD34 at day 6 appears to define the onset of the primitive program, as the majority of the primitive erythroid progenitors are derived from this population. The fact that both programs develop from a CD34$^+$ progenitor, clearly indicates that this marker is not sufficient for monitoring the development of hematopoiesis in the PSC differentiation cultures and highlights the need for identifying new surface markers that distinguish primitive and definitive progenitors at the earliest stages of development.

Manipulation of the Activin/nodal signaling pathway with the small molecule SB-431542 in this study has provided novel insights into its role in the establishment of the hematopoietic system in hESC cultures, as well as into the origin of human definitive hematopoiesis. SB-431542 has been identified as a highly potent and selective inhibitor of the Activin/nodal pathway, with no observed inhibition of other pathways or kinases including BMP4, ERK, JNK or p38 MAPK {Inman, 2002 #48}. Our demonstration that SB reduces phospho-Smad2 levels in day 2 EBs (FIG. 4B) and that it has opposing effects to that of Activin A on erythroid colony formation (FIG. 1B) provide strong evidence that its effect on the primitive erythroid lineage is mediated through inhibition of the Activin/nodal pathway and not an unknown target. Previous studies have demonstrated that the Activin/nodal, in addition to BMP-4 and Wnt pathways all play a role in the early induction steps in hPSC cultures, including primitive streak formation, mesoderm induction and hematopoietic specification (Davis et al., 2008; Jackson et al., 2010; Kennedy et al., 2007; Kroon et al., 2008; Sumi et al., 2008; Vijayaragavan et al., 2009). The staged addition of the Activin/nodal pathway inhibitor in this report reinforces a role for this pathway in the early stages of development, as addition between days 1 and 2 of differentiation prevented the development of any KDR$^+$ cells, indicating a lack of mesoderm formation. Additionally, our study documents a previously unidentified requirement for Activin/nodal signaling at the earliest stages of human primitive hematopoietic development. In this regard, mouse and human primitive hematopoiesis appear to be regulated similarly, as previous studies have indicated that this pathway is also required for mouse primitive hematopoietic development (Nostro et al., 2008, Pearson et al., 2008). While our Western analyses demonstrate the presence of phospho-SMAD 2 indicative of Activin/nodal signaling in the day 2 EBs, the interacting and/or downstream pathways mediating this effect are currently unknown. Addition of agonists and/or antagonists of other pathways including Wnt, Notch and SHH together with SB between day 2 and 4 of differentiation had little impact on the inhibitory effect suggesting that they are not directly involved in mediating this effect (data not shown).

In addition to blocking primitive hematopoiesis, the addition of SB at early stages of differentiation also appeared to impact the potential of the CD34$^+$ population. The SB-treated CD34$^+$ population expressed higher levels of SOX17 and AML1C and contained a higher frequency of erythroid and T-cell progenitors than the corresponding Activin A-induced population. These observations clearly demonstrate that manipulation of signaling pathways at early stages of differentiation can impact the potential of later stage cells and as such highlight the importance of using defined induction conditions and precise stage-specific protocols for such studies.

In summary, the findings reported here have identified a definitive hematopoietic progenitor population that displays T-lymphoid, myeloid and erythroid potential as well as surface markers and gene expression patterns indicative of a pre-HSC population. We hypothesize that the definitive progenitors identified here represents the first step in the generation of HSCs from hPSCs and as such, provide a readily accessible target population for defining the regulatory pathways that control its specification to the earliest hematopoietic progenitors and maturation to transplantable stem cells. In addition to providing a marker for definitive hematopoiesis, the ability to generate T cells from hPSCs under defined induction conditions offers unique opportunities to investigate the developmental origins of this lineage, as well as the functional potential of the cells in in vitro and in vivo models.

Although preferred embodiments of the invention have been described herein, it will be understood by those skilled in the art that variations may be made thereto without departing from the spirit of the invention or the scope of the appended claims. All documents disclosed herein are incorporated by reference.

REFERENCES

Andersson, L. C., von Willebrand, E., Jokinen, M., Karhi, K. K., and Gahmberg, C. G. (1981). Glycophorin A as an erythroid marker in normal and malignant hematopoiesis. Haematology and blood transfusion 26, 338-344.

Awong, G., Herer, E., Surh, C. D., Dick, J. E., La Motte-Mohs, R. N., and Zuniga-Pflucker, J. C. (2009). Characterization in vitro and engraftment potential in vivo of human progenitor T cells generated from hematopoietic stem cells. Blood 114, 972-982.

Bertrand, J. Y., Giroux, S., Golub, R., Klaine, M., Jalil, A., Boucontet, L., Godin, I., and Cumano, A. (2005). Characterization of purified intraembryonic hematopoietic stem cells as a tool to define their site of origin. Proceedings of the National Academy of Sciences of the United States of America 102, 134-139.

Chadwick, K., Wang, L., Li, L., Menendez, P., Murdoch, B., Rouleau, A., and Bhatia, M. (2003). Cytokines and BMP-4 promote hematopoietic differentiation of human embryonic stem cells. Blood 102, 906-915.

Choi, K. D., Vodyanik, M. A., Togarrati, P. P., Suknuntha, K., Kumar, A., Samarjeet, F., Probasco, M. D., Tian, S., Stewart, R., Thomson, J. A., et al. (2012). Identification of the hemogenic endothelial progenitor and its direct precursor in human pluripotent stem cell differentiation cultures. Cell reports 2, 553-567.

Conlon, F. L., Lyons, K. M., Takaesu, N., Barth, K. S., Kispert, A., Herrmann, B., and Robertson, E. J. (1994). A primary requirement for nodal in the formation and maintenance of the primitive streak in the mouse. Development (Cambridge, England) 120, 1919-1928.

Davis, R. P., Ng, E. S., Costa, M., Mossman, A. K., Sourris, K., Elefanty, A. G., and Stanley, E. G. (2008). Targeting a GFP reporter gene to the MIXL1 locus of human embryonic stem cells identifies human primitive streak-like cells and enables isolation of primitive hematopoietic precursors. Blood 111, 1876-1884.

Doulatov, S., Notta, F., Eppert, K., Nguyen, L. T., Ohashi, P. S., and Dick, J. E. (2010). Revised map of the human progenitor hierarchy shows the origin of macrophages and dendritic cells in early lymphoid development. Nat Immunol 11, 585-593.

Dzierzak, E., and Speck, N. A. (2008). Of lineage and legacy: the development of mammalian hematopoietic stem cells. Nat Immunol 9, 129-136.

Feugier, P., Li, N., Jo, D. Y., Shieh, J. H., MacKenzie, K. L., Lesesve, J. F., Latger-Cannard, V., Bensoussan, D., Crystal, R. G., Rafii, S., et al. (2005). Osteopetrotic mouse stroma with thrombopoietin, c-kit ligand, and flk-2 ligand supports long-term mobilized CD34+ hematopoiesis in vitro. Stem cells and development 14, 505-516.

Funaro, A., Spagnoli, G. C., Ausiello, C. M., Alessio, M., Roggero, S., Delia, D., Zaccolo, M., and Malavasi, F. (1990). Involvement of the multilineage CD38 molecule in a unique pathway of cell activation and proliferation. J Immunol 145, 2390-2396.

Galic, Z., Kitchen, S. G., Kacena, A., Subramanian, A., Burke, B., Cortado, R., and Zack, J. A. (2006). T lineage differentiation from human embryonic stem cells. Proceedings of the National Academy of Sciences of the United States of America 103, 11742-11747.

Groth, F. d. S. (1982). The evaluation of limiting dilution assays. Journal of Immunological Methods 49, R11-23.

Hong, S. H., Lee, J. H., Lee, J. B., Ji, J., and Bhatia, M. (2011). ID1 and ID3 represent conserved negative regulators of human embryonic and induced pluripotent stem cell hematopoiesis. J Cell Sci 124, 1445-1452.

Inman, G. J., Nicolas, F. J., Callahan, J. F., Harling, J. D., Gaster, L. M., Reith, A. D., Laping, N. J., and Hill, C. S. (2002). SB-431542 is a potent and specific inhibitor of transforming growth factor-beta superfamily type I activin receptor-like kinase (ALK) receptors ALK4, ALK5, and ALK7. Mol Pharmacol 62, 65-74.

Irion, S., Clarke, R. L., Luche, H., Kim, I., Morrison, S. J., Fehling, H. J., and Keller, G. M. (2010). Temporal specification of blood progenitors from mouse embryonic stem cells and induced pluripotent stem cells. Development (Cambridge, England) 137, 2829-2839.

Ivanovs, A., Rybtsov, S., Welch, L., Anderson, R. A., Turner, M. L., and Medvinsky, A. (2012). Highly potent human hematopoietic stem cells first emerge in the intraembryonic aorta-gonad-mesonephros region. Journal of Experimental Medicine 208, 2417-2427

Jackson, S. A., Schiesser, J., Stanley, E. G., and Elefanty, A. G. (2010). Differentiating embryonic stem cells pass through 'temporal windows' that mark responsiveness to exogenous and paracrine mesendoderm inducing signals. PLoS One 5, e10706.

June, C. H., Ledbetter, J. A., Linsley, P. S., and Thompson, C. B. (1990). Role of the CD28 receptor in T-cell activation. Immunology today 11, 211-216.

Kaufman, D. S., Hanson, E. T., Lewis, R. L., Auerbach, R., and Thomson, J. A. (2001). Hematopoietic colony-forming cells derived from human embryonic stem cells. Proceedings of the National Academy of Sciences of the United States of America 98, 10716-10721.

Kennedy, M., D'Souza, S. L., Lynch-Kattman, M., Schwantz, S., and Keller, G. (2007). Development of the hemangioblast defines the onset of hematopoiesis in human ES cell differentiation cultures. Blood 109, 2679-2687.

Klimchenko, O., Mori, M., Distefano, A., Langlois, T., Larbret, F., Lecluse, Y., Feraud, O., Vainchenker, W., Norol, F., and Debili, N. (2009). A common bipotent progenitor generates the erythroid and megakaryocyte lineages in embryonic stem cell-derived primitive hematopoiesis. Blood 114, 1506-1517.

Kroon, E., Martinson, L. A., Kadoya, K., Bang, A. G., Kelly, O. G., Eliazer, S., Young, H., Richardson, M., Smart, N. G., Cunningham, J., et al. (2008). Pancreatic endoderm derived from human embryonic stem cells generates glucose-responsive insulin-secreting cells in vivo. Nature biotechnology 26, 443-452.

La Motte-Mohs, R. N., Herer, E., and Zuniga-Pflucker, J. C. (2005). Induction of T-cell development from human cord blood hematopoietic stem cells by Delta-like 1 in vitro. Blood 105, 1431-1439.

Labastie, M. C., Cortes, F., Romeo, P. H., Dulac, C., and Peault, B. (1998). Molecular identity of hematopoietic precursor cells emerging in the human embryo. Blood 92, 3624-3635.

Ledran, M. H., Krassowska, A., Armstrong, L., Dimmick, I., Renstrom, J., Lang, R., Yung, S., Santibanez-Coref, M., Dzierzak, E., Stojkovic, M., et al. (2008). Efficient hematopoietic differentiation of human embryonic stem cells on stromal cells derived from hematopoietic niches. Cell stem cell 3, 85-98.

Lu, M., Kardel, M. D., O'Connor, M. D., and Eaves, C. J. (2009). Enhanced generation of hematopoietic cells from human hepatocarcinoma cell-stimulated human embryonic and induced pluripotent stem cells. Experimental hematology 37, 924-936.

Marshall, C. J., Moore, R. L., Thorogood, P., Brickell, P. M., Kinnon, C., and Thrasher, A. J. (1999). Detailed characterization of the human aorta-gonad-mesonephros region reveals morphological polarity resembling a hematopoietic stromal layer. Dev Dyn 215, 139-147.

Murry, C. E., and Keller, G. (2008). Differentiation of embryonic stem cells to clinically relevant populations: lessons from embryonic development. Cell 132, 661-680.

Ng, E. S., Azzola, L., Sourris, K., Robb, L., Stanley, E. G., and Elefanty, A. G. (2005). The primitive streak gene Mixl1 is required for efficient haematopoiesis and BMP4-induced ventral mesoderm patterning in differentiating ES cells. Development (Cambridge, England) 132, 873-884.

Nostro, M. C., Cheng, X., Keller, G. M., and Gadue, P. (2008). Wnt, activin, and BMP signaling regulate distinct stages in the developmental pathway from embryonic stem cells to blood. Cell stem cell 2, 60-71.

Notta, F., Doulatov, S., Laurenti, E., Poeppl, A., Jurisica, I., and Dick, J. E. (2011). Isolation of single human hematopoietic stem cells capable of long-term multilineage engraftment. Science (New York, N. Y. 333, 218-221.

Oberlin, E., Tavian, M., Blazsek, I., and Peault, B. (2002). Blood-forming potential of vascular endothelium in the human embryo. Development (Cambridge, England) 129, 4147-4157.

Palis, J., Malik, J., McGrath, K. E., and Kingsley, P. D. (2010). Primitive erythropoiesis in the mammalian embryo. The International journal of developmental biology 54, 1011-1018.

Park, I. H., Zhao, R., West, J. A., Yabuuchi, A., Huo, H., Ince, T. A., Lerou, P. H., Lensch, M. W., and Daley, G. Q. (2008). Reprogramming of human somatic cells to pluripotency with defined factors. Nature 451, 141-146.

Pearson, S., Sroczynska, P., Lacaud, G., and Kouskoff, V. (2008). The stepwise specification of embryonic stem cells to hematopoietic fate is driven by sequential exposure to Bmp4, activin A, bFGF and VEGF. Development (Cambridge, England) 135, 1525-1535.

Phillips, D. R., Charo, I. F., Parise, L. V., and Fitzgerald, L. A. (1988). The platelet membrane glycoprotein IIb-IIIa complex. Blood 71, 831-843.

Pick, M., Azzola, L., Mossman, A., Stanley, E. G., and Elefanty, A. G. (2007). Differentiation of human embryonic stem cells in serum-free medium reveals distinct roles for bone morphogenetic protein 4, vascular endothelial growth factor, stem cell factor, and fibroblast growth factor 2 in hematopoiesis. Stem Cells 25, 2206-2214.

Rhodes, K. E., Gekas, C., Wang, Y., Lux, C. T., Francis, C. S., Chan, D. N., Conway, S., Orkin, S. H., Yoder, M. C., and Mikkola, H. K. (2008). The emergence of hematopoietic stem cells is initiated in the placental vasculature in the absence of circulation. Cell stem cell 2, 252-263.

Schmitt, T. M., de Pooter, R. F., Gronski, M. A., Cho, S. K., Ohashi, P. S., and Zuniga-Pflucker, J. C. (2004). Induction of T cell development and establishment of T cell competence from embryonic stem cells differentiated in vitro. Nat Immunol 5, 410-417.

Schuh, K., Twardzik, T., Kneitz, B., Heyer, J., Schimpl, A., and Serfling, E. (1998). The interleukin 2 receptor alpha chain/CD25 promoter is a target for nuclear factor of activated T cells. The Journal of experimental medicine 188, 1369-1373.

Sumi, T., Tsuneyoshi, N., Nakatsuji, N., and Suemori, H. (2008). Defining early lineage specification of human embryonic stem cells by the orchestrated balance of canonical Wnt/beta-catenin, Activin/Nodal and BMP signaling. Development (Cambridge, England) 135, 2969-2979.

Taoudi, S., and Medvinsky, A. (2007). Functional identification of the hematopoietic stem cell niche in the ventral domain of the embryonic dorsal aorta. Proceedings of the National Academy of Sciences of the United States of America 104, 9399-9403.

Tavian, M., Biasch, K., Sinka, L., Vallet, J., and Peault, B. (2010). Embryonic origin of human hematopoiesis. The International journal of developmental biology 54, 1061-1065.

Tavian, M., Robin, C., Coulombel, L., and Peault, B. (2001). The human embryo, but not its yolk sac, generates lympho-myeloid stem cells: mapping multipotent hematopoietic cell fate in intraembryonic mesoderm. Immunity 15, 487-495.

Thomson, J. A., Itskovitz-Eldor, J., Shapiro, S. S., Waknitz, M. A., Swiergiel, J. J., Marshall, V. S., and Jones, J. M. (1998). Embryonic stem cell lines derived from human blastocysts. Science (New York, N. Y. 282, 1145-1147.

Tian, X., Woll, P. S., Morris, J. K., Linehan, J. L., and Kaufman, D. S. (2006). Hematopoietic engraftment of human embryonic stem cell-derived cells is regulated by recipient innate immunity. Stem Cells 24, 1370-1380.

Timmermans, F., Velghe, I., Vanwalleghem, L., De Smedt, M., Van Coppernolle, S., Taghon, T., Moore, H. D., Leclercq, G., Langerak, A. W., Kerre, T., et al. (2009). Generation of T cells from human embryonic stem cell-derived hematopoietic zones. J Immunol 182, 6879-6888.

Vijayaragavan, K., Szabo, E., Bosse, M., Ramos-Mejia, V., Moon, R. T., and Bhatia, M. (2009). Noncanonical Wnt signaling orchestrates early developmental events toward hematopoietic cell fate from human embryonic stem cells. Cell stem cell 4, 248-262.

Vodyanik, M. A., Thomson, J. A., and Slukvin, I I (2006). Leukosialin (CD43) defines hematopoietic progenitors in human embryonic stem cell differentiation cultures. Blood 108, 2095-2105.

Wang, L., Li, L., Shojaei, F., Levac, K., Cerdan, C., Menendez, P., Martin, T., Rouleau, A., and Bhatia, M. (2004). Endothelial and hematopoietic cell fate of human embryonic stem cells originates from primitive endothelium with hemangioblastic properties. Immunity 21, 31-41.

Wang, L., Menendez, P., Shojaei, F., Li, L., Mazurier, F., Dick, J. E., Cerdan, C., Levac, K., and Bhatia, M. (2005). Generation of hematopoietic repopulating cells from human embryonic stem cells independent of ectopic HOXB4 expression. The Journal of experimental medicine 201, 1603-1614.

Yokomizo, T., and Dzierzak, E. (2010). Three-dimensional cartography of hematopoietic clusters in the vasculature of whole mouse embryos. Development (Cambridge, England) 137, 3651-3661.

Yoshimoto, M., Montecino-Rodriguez, E., Ferkowicz, M. J., Porayette, P., Shelley, W. C., Conway, S. J., Dorshkind, K., and Yoder, M. C. (2011). Embryonic day 9 yolk sac and intra-embryonic hemogenic endothelium independently generate a B-1 and marginal zone progenitor lacking B-2 potential. Proceedings of the National Academy of Sciences of the United States of America 108, 1468-1473.

Yoshimoto, M., Porayette, P., Glosson, N. L., Conway, S. J., Carlesso, N., Cardoso, A. A., Kaplan, M. H., and Yoder, M. C. (2012). Autonomous murine T-cell progenitor production in the extra-embryonic yolk sac before HSC emergence. Blood 119, 5706-5714.

Yu, C., Liu, Y., Miao, Z., Yin, M., Lu, W., Lv, Y., Ding, M., and Deng, H. (2010). Retinoic acid enhances the generation of hematopoietic progenitors from human embryonic stem cell-derived hemato-vascular precursors. Blood 116, 4786-4794.

Zambidis, E. T., Peault, B., Park, T. S., Bunz, F., and Civin, C. I. (2005). Hematopoietic differentiation of human embryonic stem cells progresses through sequential hematoendothelial, primitive, and definitive stages resembling human yolk sac development. Blood 106, 860-870.

The invention claimed is:

1. A method of enriching a population of stem cells for hematopoietic progenitors from a population of human pluripotent stem cells that have been induced to undergo hematopoietic differentiation, the method comprising:
   a. inducing hematopoietic differentiation in a population of human pluripotent stem cells, wherein activin/nodal signaling is inhibited between day 1 and day 4 of differentiation;
   b. sorting the induced population based on expression of CD34 and CD43; and
   c. selecting a fraction of the cell population that is CD34$^+$CD43$^-$, and
wherein the sorting and cell fraction selection is performed on a day selected from about day 6 to about day 11 of differentiation.

2. The method of claim 1, wherein inducing hematopoietic differentiation is conducted serum free.

3. The method of claim 1, wherein inducing hematopoietic differentiation is conducted stroma free.

4. The method of claim 1, wherein inducing hematopoietic differentiation comprises culturing the population with BMP4.

5. The method of claim 1, wherein inducing hematopoietic differentiation comprises culturing the population with bFGF.

6. The method of claim 1, wherein inducing hematopoietic differentiation comprises culturing the population with at least one of VEGF, DKK, IL-6 and IL-11, and/or combinations thereof, between days 3 and 11, or between days 4 and 9.

7. The method of claim 1, wherein inducing hematopoietic differentiation comprises culturing the population with at least one of SCF and EPO, between days 4 and 11, or between days 6 and 9.

8. The method of claim 1, wherein inducing hematopoietic differentiation comprises culturing the population with at least one of TPO, Flt-3 and IL-3, and/or combinations thereof, between days 6 and 11, or and 8 and 9.

9. The method of claim 1, wherein inhibiting activin/nodal signaling comprises culturing the population with an activin/nodal inhibitor.

10. The method of claim 9, wherein the inhibitor is SB-431542.

11. The method of claim 1, wherein the fraction comprises at least 10%, 20%, 30%, 40%, 50%, 60%, 70%, 80%, 90% or 100% hematopoietic progenitors.

12. The method of claim 10, wherein the population is cultured with between 1 µM to 10 mM, 1 µM to 1 mM, or about 6 µM SB-431542.

13. The method of claim 1, wherein activin/nodal signaling is inhibited between day 2 and day 4 of differentiation.

14. The method of claim 13, wherein activin/nodal signaling is inhibited by culturing the population is cultured with between 1 µM to 10 mM, 1 µM to 1 mM, or about 6 µM SB-431542.

* * * * *